United States Patent [19]
Sloma et al.

[11] Patent Number: 5,958,728
[45] Date of Patent: Sep. 28, 1999

[54] METHODS FOR PRODUCING POLYPEPTIDES IN MUTANTS OF BACILLUS CELLS

[75] Inventors: Alan Sloma; David Sternberg; Lee F. Adams; Stephen Brown, all of Davis, Calif.

[73] Assignee: Novo NordiskBiotech, Inc., Davis, Calif.

[21] Appl. No.: 08/972,661

[22] Filed: Nov. 18, 1997

Related U.S. Application Data

[60] Provisional application No. 60/049,441, Jun. 12, 1997, and provisional application No. 60/086,231, Nov. 18, 1996.

[51] Int. Cl.$^6$ ............................... C12N 1/21; C12P 21/00
[52] U.S. Cl. ..................................... 435/69.1; 435/252.31; 435/471; 435/477; 435/485
[58] Field of Search ................... 435/69.1, 172.3, 435/252.31, 471, 485, 477

[56] References Cited

FOREIGN PATENT DOCUMENTS 0 576 050 A1  12/1993  European Pat. Off. .
WO 91/02792   3/1991   WIPO .

OTHER PUBLICATIONS

Nakano et al., Mol. Gen. Genet. 232:313–321 (1992).
D'Souza et al., J. Bact. 175(11):3502–3510 (1993).
Vollenbroich et al., J. Bact. 176(2):395–400 (1994).
Galli et al., "Characterization of the Surfactin Synthetase Multi–Enzyme Complex", Biochinica et Biophsica Acta vol. 1205 (1994) pp. 19–28.
Razafindralambo et al. "Foaming Properties of Surfactin, a Lipopeptide Biosurfactant From *Bacillus Subtilis*", JAOCS, vol. 73, No. 1, (1996), pp. 149–151.
Database WPI, Section Ch, Week 7417, Derwent Publications Ltd., London, GB; AN 74–31507V — XP002058920 & JP 49001 791 A (Nat Res Inst of Brewing), Jan. 9, 1974.

*Primary Examiner*—Johnny F. Railey, II
*Attorney, Agent, or Firm*—Steven T. Zelson; Elias J Lambiris; Valeta A. Gregg

[57] ABSTRACT

The present invention relates to methods of producing a polypeptide, comprising: (a) cultivating a mutant of a Bacillus cell, wherein the mutant (i) comprises a first nucleic acid sequence encoding the polypeptide and a second nucleic acid sequence comprising a modification of at least one of the genes responsible for the biosynthesis or secretion of a surfactin or isoform thereof under conditions conducive for the production of the polypeptide and (ii) the mutant produces less of the surfactin or isoform thereof than the Bacillus cell when cultured under the same conditions; and (b) isolating the polypeptide from the cultivation medium. The present invention also relates to mutants of Bacillus cells and methods for producing the mutants.

29 Claims, 8 Drawing Sheets

METHODS FOR PRODUCING POLYPEPTIDES IN MUTANTS OF BACILLUS CELLS

CROSS-REFERENCE TO RELATED APPLICATIONS

This applications claims priority of U.S. provisional application No. 60/049,441 filed Jun. 12, 1997 and U.S. provisional application No. 60/086,231, filed Nov. 18, 1996, the contents of which are fully incorporated herein by reference.

BACKGROUND OF THE INVENTION

1. Field of the Invention

The present invention relates to methods of producing polypeptides in a mutant of a Bacillus cell, methods of obtaining the mutants of Bacillus cells, and the mutants of Bacillus cells.

2. Description of the Related Art

Surfactin is a cyclic lipopeptide with remarkable surfactant properties which is produced primarily during the stationary phase of growth by several species of Bacillus (Carswell et al., 1994, *Applied Microbiology and Biotechnology* 41: 281–285; Lin et al., 1994, *Applied and Environmental Microbiology* 60: 31–38; Morikawa et al., 1992, *Journal of Fermentation and Bioenginnering* 74: 255–261; Arima et al., 1968, *Biochemical Biophysical Research Communications* 31: 488–494). The lipopeptide contains seven amino acids, L-Glu-L-Leu-D-Leu-L-Val-L-Asp-D-Leu-L-Leu (SEQ ID NO:35) linked to 3-hydroxy-13-methyltetradecanoic acid through an amide bond between the carboxy group of the fatty acid and the amino group of glutamic acid and an ester bond between the carboxyl group of the last Leu and the hydroxyl group of the fatty acid. A homologous series with lipidic chainlengths of 13, 14, and 15 carbons (Hosono and Suzuki, 1983, *Journal of Antibiotics* 36: 667–673; Razafindralambo et al., 1993, *Journal of Chromatography* 639: 81–85), and isoforms named [Val7]-, [Ile7]-, and [Ala4]-surfactin differing by the seventh or the fourth amino acid (Peypoux et al., 1994, *European Journal of Biochemistry* 224: 89–96; Baugmart et al., 1991, *Biochemical Biophysical Research Communications* 177: 998–1005) are known.

A multienzyme complex encoded by the srf operon is reportedly responsible for the nonribosomal biosynthesis of surfactin via the so-called thiotemplate mechanism. The operon contains at least four genes, srfA, srfB, srfC, and srfD. The genes srfA, srfB, srfC, and srfD were previously known as srfAA, srfAB, srfAC, and srfAD, respectively. SrfA, srfB and srfC encode the surfactin synthetase subunits, each containing one or more amino acid-activating domains necessary for the activation of the surfactin substrate amino acids to produce surfactin (van Sinderen et al., 1993, *Molecular Microbiology* 8: 833–841; Nakano and Zuber, 1989, *Journal of Bacteriology* 8: 821–831; Cosmina et al., 1993, *Molecular Microbiology* 8:821–831). The multienzyme complex is organized in seven large domains clustered on three separate proteins (Menkhaus et al., 1993, *Journal of Biological Chemistry* 268: 7678–7684; Gulli et al., *Biochimica et Biophysica Acta* 1205: 19–28). The seven domains are responsible for the activation and binding of the seven amino acids of surfactin. According to the thiotemplate mechanism, the adenylation and binding of a specific amino acid take place at the corresponding amino acid-activating domain, a process which requires the cofactor 4-phosphopantetheine. Subsequent trans-thioesterification reactions result in a growing peptide chain, the order of which is determined by the spatial arrangement of the multienzyme subunits. It is currently not known how and when the fatty acid moiety is linked to the peptide and how the ester bond is formed to make the molecule cyclic. Furthermore, the gene sfp is thought to be involved in expression (secretion) of surfactin (Nakano et al., 1992, *Molecular General Genetics* 232: 313–323).

Bacilli are well established as host cell systems for the production of native and recombinant proteins. However, Bacillus hosts with the desirable traits of increased protein expression and secretion may not necessarily have the most desirable characteristics for successful fermentation. Specifically, the fermentation may not be optimal because of an increase in foaming as biomass increases. Increased foaming limits the productivity of the fermentation.

It is therefore an object of the present invention to provide improved Bacillus hosts which combine the capacity for expression of commercial quantities of protein with satisfactory fermentation characteristics, such as rapid growth and low foaming, thereby enhancing fermentative productivity.

SUMMARY OF THE INVENTION

The present invention relates to methods of producing a polypeptide, comprising: (a) cultivating a mutant of a Bacillus cell, wherein (i) the mutant comprises a first nucleic acid sequence encoding the polypeptide and a second nucleic acid sequence comprising a modification of at least one of the genes responsible for the biosynthesis or secretion of a surfactin or isoform thereof under conditions conducive for the production of the polypeptide and (ii) the mutant produces less of the surfactin or isoform thereof than the Bacillus cell when cultured under the same conditions; and (b) isolating the polypeptide from the cultivation medium.

The present invention also relates to mutants of Bacillus cells and methods of obtaining the mutants of Bacillus cells.

DETAILED DESCRIPTION OF THE INVENTION

Figure 1:
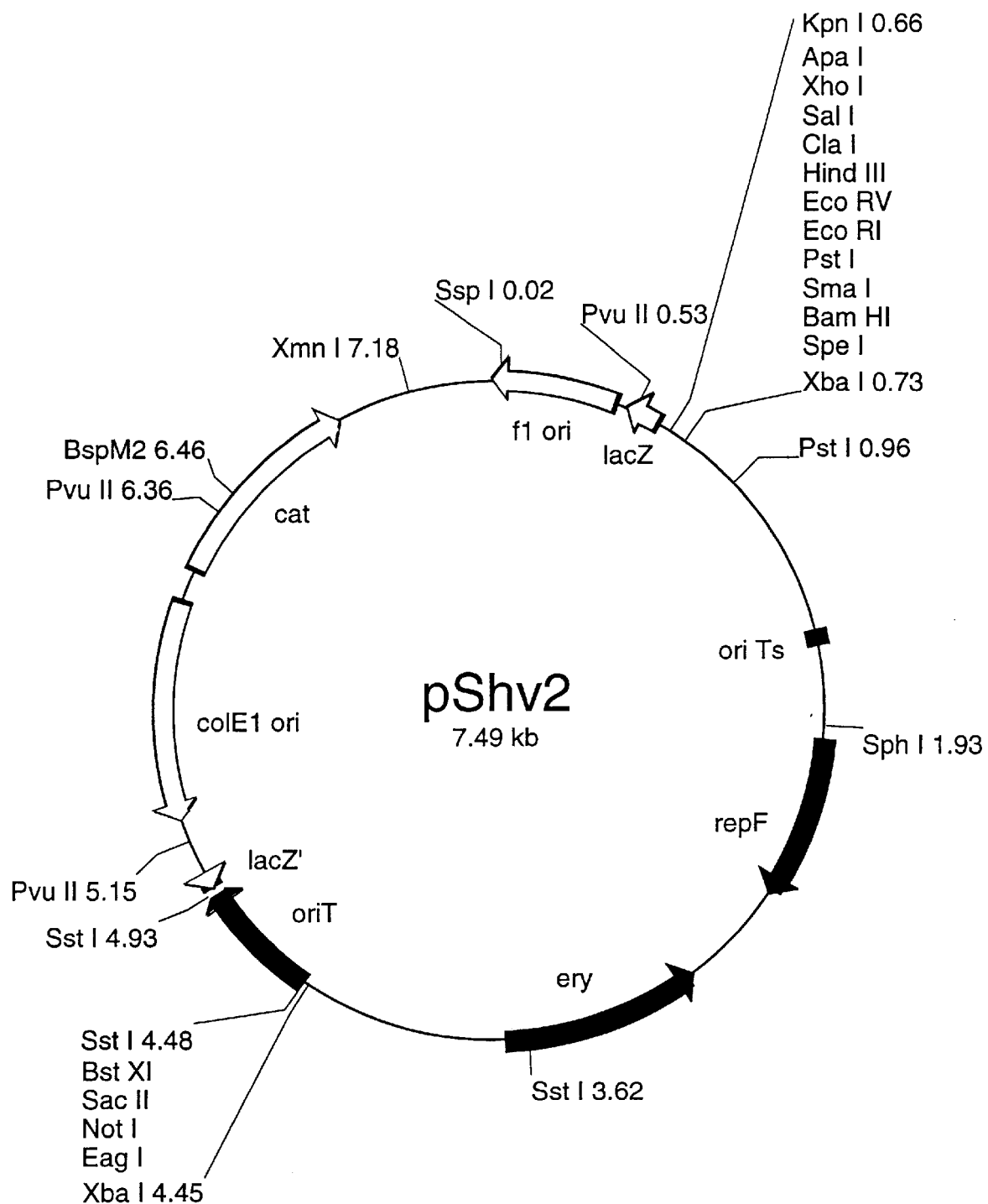
FIG. 1 shows a restriction map of pShv2.

The present invention relates to methods of producing a polypeptide, comprising: (a) cultivating a mutant of a Bacillus cell, wherein (i) the mutant relates to the Bacillus cell by the modification, e.g., disruption, of at least one of the genes responsible for the biosynthesis or secretion of a surfactin or isoform thereof under conditions conducive for the production of the polypeptide and (ii) the mutant produces less of the surfactin or isoform thereof than the Bacillus cell when cultured under the same conditions; and (b) isolating the polypeptide from the cultivation medium.

The term "surfactin" is defined herein as a cyclic lipopeptide with an amino acid sequence L-Glu-L-Leu-D-Leu-L-Val-L-Asp-D-Leu-L-Leu (SEQ ID NO:35) linked to a straight or branched b-hydroxy fatty acid with a varying chain length of 13–15 carbon atoms. The term "isoform" is defined herein as variants of a surfactin in which one or more amino acid residues have been substituted with a different amino acid residue, e.g., [Val7]-, [Ile7]-, and [Ala4]-surfactin.

In the methods of the present invention, the Bacillus cell may be a wild-type Bacillus cell or a mutant thereof. Bacillus cells useful in the practice of the present invention include, but are not limited to, *Bacillus alkalophilus, Bacillus amyloliquefaciens, Bacillus brevis, Bacillus circulans, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells. In a preferred embodiment, the Bacillus cell is a *Bacillus amyloliquefaciens, Bacillus lentus, Bacillus licheniformis, Bacillus stearothermophilus* or *Bacillus subtilis* cell. In a more preferred embodiment, the Bacillus cell is *Bacillus subtilis* ATCC 6051 or 6051A or *Bacillus subtilis* NCFB 736 (formerly NCDO 736).

The mutants of Bacillus cells may be constructed by reducing or eliminating expression of one or more genes responsible for the biosynthesis or secretion of the surfactin or isoform thereof using methods well known in the art for insertions or deletions. For example, one of the genes may be disrupted by inserting into the gene an integrative plasmid containing a nucleic acid fragment homologous to the gene which will create a duplication of the region of homology and incorporate vector DNA between the duplicated regions. This can eliminate gene expression if the inserted vector separates the promoter of the gene from the coding region or interrupts the coding sequence such that a non-functional gene product results. In addition, one or more of the control sequences which are necessary or advantageous for expression of one or more of the genes responsible for the biosynthesis or secretion of a surfactin or isoform thereof, e.g., promoter, may be modified. Alternatively, gene expression may be reduced or eliminated by the process of gene conversion (see, for example, Iglesias and Trautner, 1983, *Molecular General Genetics* 189: 73–76) or by gene replacement. In the latter process, a mutated version of the gene is introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene (see, for example, Perego, 1993, In A. L. Sonneshein, J. A. Hoch, and R. Losick, editors, *Bacillus subtilis* and *Other Gram-Positive Bacteria*, Chapter 42, American Society of Microbiology, Washington, D.C., 1993). Furthermore, reduction or elimination of expression of one or more genes responsible for the biosynthesis or secretion of the surfactin may be accomplished by random mutagenesis using methods well known in the art, including, but not limited to, transposition and chemical mutagenesis.

The mutants of Bacillus cells may also be constructed to produce a variant or isoform of surfactin. The variant or isoform will differ from the peptide isolated from its native source in that the variant is non-foaming or has reduced surfactant properties. Modification of a nucleic acid sequence of one or more genes responsible for the biosynthesis of surfactin may be accomplished by methods well known in the art, e.g., exchange of domain coding regions leading to the construction of hybrid genes that encode peptide synthethases with altered amino acid specificities and the production of peptides with modified amino acid sequences (see, for example, Stachelhaus et al., 1995, *Science* 269: 60–72). In a further aspect of the present invention, the amino acid substitution may confer a surfactin-negative phenotype such as a Ser-to-Ala substitution (D'Souza et al., 1993, *Journal of Bacteriology* 175: 3502–3510; Vollenbroich et al., 1993, *FEBS Letters* 325: 220–224; Stachelhaus et al., 1995, supra). The analogous nucleic acid sequence may be constructed on the basis of the nucleic acid sequences of the genes responsible for the biosynthesis of the surfactin lipopeptide by introduction of nucleotide substitutions which results in a different amino acid sequence than the amino acid sequence of the native surfactin molecule. For a general description of nucleotide substitution, see, e.g., Ford et al., 1991, *Protein Expression and Purification* 2:95–107.

It will be apparent to those skilled in the art that such substitutions can be made outside and within the regions critical to the function of the molecule. Amino acid residues essential to the surfactant property of the peptide may be identified according to procedures known in the art, such as site-directed mutagenesis or alanine-scanning mutagenesis (see, e.g., Cunningham and Wells, 1989, *Science* 244:1081–1085). In the latter technique, mutations are introduced at every residue in the molecule, and the resultant mutant molecules are tested for surfactant activity to identify amino acid residues that are critical to the activity of the molecule.

In the methods of the present invention, any gene of a Bacillus cell responsible for the biosynthesis or secretion of a surfactin or isoform thereof may be modified. For example, the gene may be any gene of the srf operon, e.g., srfA, srfB, srfC and srfD. Alternatively, the gene sfp may be modified.

In a further aspect of the present invention, the gene(s) responsible for linking the fatty acid moiety to the peptide or forming the ester bond to make the molecule cyclic may be the subject of the modification to render the Bacillus mutant cell deficient in foaming properties.

In an even further aspect of the present invention, the mutants of Bacillus cells additionally may contain deletions or insertions of other genes which may be detrimental to the production, recovery or application of a polypeptide. For example, in a preferred embodiment, the Bacillus cell may be a protease-deficient cell. In another preferred embodiment, the Bacillus cell does not produce spores. e.g., due to a deletion in spoIIAC. Other genes, e.g. the amyE gene, which are detrimental to the production, recovery or application of a polypeptide may be deleted.

In the methods of the present invention, the mutants of the present invention have non-foaming or reduced foaming properties when cultivated under conditions conducive for production of the polypeptide. The level of surfactin lipopeptide produced by a mutant of a Bacillus cell of the present invention may be determined using methods well known in the art (see, for example, Ohno et al., 1995, *Biotechnology and Bioengineering* 47: 209–214 and Grossman et al., 1993, *Journal of Bacteriology* 175: 6203–6211). The mutant cell preferably produces at least about 25% less, more preferably at least about 50% less, even more preferably at least about 75% less, and most preferably at least about 95% less surfactin lipopeptide than a corresponding parent Bacillus cell when cultured under identical production conditions. The mutant cell preferably produces at least about 25% more, more preferably at least about 50% more, even more preferably at least about 75% more, and most preferably at least about 95% more of the polypeptide than a corresponding parent Bacillus cell when cultured under identical production conditions.

The cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted polypeptide can be recovered directly from the medium.

The polypeptides may be detected using methods known in the art that are specific for the polypeptides. These detection methods may include use of specific antibodies, formation of an enzyme product, disappearance of an enzyme substrate, or SDS-PAGE. For example, an enzyme assay may be used to determine the activity of the polypeptide. Procedures for determining enzyme activity are known in the art for many enzymes.

The resulting polypeptide may be isolated by methods known in the art. For example, the polypeptide may be isolated from the nutrient medium by conventional procedures including, but not limited to, centrifugation, filtration, extraction, spray-drying, evaporation, or precipitation. The isolated polypeptide may then be further purified by a variety of chromatographic procedures, e.g., ion exchange chromatography, gel filtration chromatography, affinity chromatography, or the like.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989).

The polypeptide may be any polypeptide. Furthermore, the polypeptide may be native or heterologous to the Bacillus cell. The term "polypeptide" is not meant herein to refer to a specific length of the encoded product and, therefore, encompasses peptides, oligopeptides, and proteins. The term "polypeptide" also encompasses two or more polypeptides combined to form the encoded product. Polypeptides also include hybrid polypeptides which comprise a combination of partial or complete polypeptide sequences obtained from at least two different polypeptides wherein one or more may be heterologous to the Bacillus cell. Polypeptides further include naturally occurring allelic and engineered variations of the above mentioned polypeptides and hybrid polypeptides.

Preferably, the polypeptide is a hormone, a hormone variant, an enzyme, a receptor or a portion thereof, an antibody or a portion thereof, or a reporter. In a more preferred embodiment, the polypeptide is an oxidoreductase, a transferase, a hydrolase, a lyase, an isomerase, or a ligase. In an even more preferred embodiment, the polypeptide is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, a pectinolytic enzyme, peroxidase, phytase, polyphenoloxidase, proteolytic enzyme, ribonuclease, transglutaminase or xylanase.

In the methods of the present invention, the mutant of the Bacillus cell may be a recombinant cell, comprising a nucleic acid sequence encoding a heterologous polypeptide, which is advantageously used in the recombinant production of the polypeptide. The cell is preferably transformed with a vector comprising the nucleic acid sequence encoding the heterologous polypeptide followed by integration of the vector into the chromosome. "Transformation" means introducing a vector comprising the second nucleic acid sequence into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the chromosome occurs by homologous recombination, non-homologous recombination or transposition.

The nucleic acid sequence encoding a heterologous polypeptide may be obtained from any prokaryotic, eukaryotic, or other source, e.g., archaeabacteria. For purposes of the present invention, the term "obtained from" as used herein in connection with a given source shall mean that the polypeptide is produced by the source or by a cell in which a gene from the source has been inserted.

In the methods of the present invention, the mutants of Bacillus cells may also be used for the recombinant production of polypeptides which are native to the Bacillus cell. The native polypeptides may be recombinantly produced by, e.g., placing a gene encoding the polypeptide under the control of a different promoter to enhance expression of the polypeptide, to expedite export of a native polypeptide of interest outside the cell by use of a signal sequence, and to increase the copy number of a gene encoding the polypeptide normally produced by the Bacillus cell. The present invention also encompasses, within the scope of the term "heterologous polypeptide", such recombinant production of homologous polypeptides, to the extent that such expression involves the use of genetic elements not native to the Bacillus cell, or use of native elements which have been manipulated to function in a manner not normally occur in the host cell.

The techniques used to isolate or clone a nucleic acid sequence encoding a heterologous polypeptide are known in the art and include isolation from genomic DNA, preparation from cDNA, or a combination thereof. The cloning of the nucleic acid sequences from such genomic DNA can be effected, e.g., by using the well known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the nucleic acid sequence encoding the polypeptide, insertion of the fragment into a vector molecule, and incorporation of the recombinant vector into a Bacillus cell where multiple copies or clones of the nucleic acid sequence will be replicated. The nucleic acid sequence may be of genomic, cDNA, RNA, semisynthetic, synthetic origin, or any combinations thereof.

In the methods of the present invention, heterologous polypeptides may also include fused polypeptides in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct may be synonymous with the term expression cassette when the nucleic acid construct contains all the control sequences required for expression of a coding sequence of the present invention. The term "coding sequence" as defined herein is a sequence which is transcribed into mRNA and translated into a polypeptide of the present invention when placed under the control of the above mentioned control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

An isolated nucleic acid sequence encoding a polypeptide may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing cloning methods are well known in the art.

A nucleic acid construct comprising a nucleic acid sequence encoding a polypeptide may be operably linked to one or more control sequences capable of directing the expression of the coding sequence in a mutant of a Bacillus cell under conditions compatible with the control sequences.

The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a Bacillus cell for expression of the nucleic acid sequence. The promoter sequence contains transcription control sequences which mediate the expression of the polypeptide. The promoter may be any nucleic acid sequence which shows transcriptional activity in the Bacillus cell of choice and may be obtained from genes encoding extracellular or intracellular polypeptides either homologous or heterologous to the Bacillus cell. Examples of suitable promoters for directing the transcription of the nucleic acid constructs of the present invention, especially in a Bacillus cell, are the promoters obtained from the *E. coli* lac operon, the *Strep-* *tomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75:3727–3731), as well as the tac promoter (DeBoer et al., 1983, *Proceedings of the National Academy of Sciences USA* 80:21–25). Further promoters are described in "Useful proteins from recombinant bacteria" in *Scientific American*, 1980, 242:74–94; and in Sambrook et al., 1989, supra.

The control sequence may also be a suitable transcription terminator sequence, a sequence recognized by a Bacillus cell to terminate transcription. The terminator sequence is operably linked to the 3' terminus of the nucleic acid sequence encoding the polypeptide. Any terminator which is functional in the Bacillus cell of choice may be used in the present invention.

The control sequence may also be a suitable leader sequence, a nontranslated region of a mRNA which is important for translation by the Bacillus cell. The leader sequence is operably linked to the 5' terminus of the nucleic acid sequence encoding the polypeptide. Any leader sequence which is functional in the Bacillus cell of choice may be used in the present invention.

The control sequence may also be a signal peptide coding region, which codes for an amino acid sequence linked to the amino terminus of the polypeptide which can direct the expressed polypeptide into the cell's secretory pathway. The signal peptide coding region may be native to the polypeptide of the invention or may be obtained from foreign sources. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide coding region may be obtained from an amylase or a protease gene from a Bacillus species. However, any signal peptide coding region capable of directing the expressed polypeptide into the secretory pathway of a Bacillus cell of choice may be used in the present invention.

An effective signal peptide coding region for Bacillus cells is the signal peptide coding region obtained from the maltogenic amylase gene from Bacillus NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* prsA gene. Further signal peptides are described by Simonen and Palva, 1993, *Microbiological Reviews* 57:109–137.

In the methods of the present invention, a recombinant expression vector comprising a nucleic acid sequence, a promoter, and transcriptional and translational stop signals may be used for the recombinant production of a polypeptide. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector which can be conveniently subjected to recombinant DNA procedures and can bring about the expression of the nucleic acid sequence. The choice of the vector will typically depend on the compatibility of the vector with the Bacillus cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the Bacillus cell, is integrated into the genome and replicated together with the chromosome(s) into which it has been integrated. The vector system may be a single vector or plasmid or two or more vectors or plasmids which together contain the total DNA to be introduced into the genome of the Bacillus cell, or a transposon.

The vectors may be integrated into the Bacillus cell genome when introduced into a Bacillus cell. For integration, the vector may rely on the nucleic acid sequence encoding the polypeptide or any other element of the vector for stable integration of the vector into the genome by homologous recombination. Alternatively, the vector may contain additional nucleic acid sequences for directing integration by homologous recombination into the genome of the Bacillus cell. The additional nucleic acid sequences enable the vector to be integrated into the Bacillus cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the Bacillus cell. Furthermore, the integrational elements may be non-encoding or encoding nucleic acid sequences.

For autonomous replication, the vector may further comprise an origin of replication enabling the vector to replicate autonomously in the Bacillus cell in question. Examples of bacterial origins of replication are the origins of replication of plasmids pBR322, pUC19, pACYC177, and pACYC184 permitting replication in E. coli, and pUB110, pE194, pTA1060, and pAMβ1 permitting replication in Bacillus. The origin of replication may be one having a mutation to make its function temperature-sensitive in the Bacillus cell (see, e.g., Ehrlich, 1978, Proceedings of the National Academy of Sciences USA 75:1433).

More than one copy of a nucleic acid sequence encoding a polypeptide of the present invention may be inserted into the Bacillus cell to amplify expression of the nucleic acid sequence. Stable amplification of the nucleic acid sequence can be obtained by integrating at least one additional copy of the sequence into the Bacillus cell genome using methods well known in the art and selecting for transformants. A convenient method for achieving amplification of genomic DNA sequences is described in WO 94/14968.

The vectors preferably contain one or more selectable markers which permit easy selection of transformed cells. A selectable marker is a gene the product of which provides for biocide resistance, resistance to heavy metals, prototrophy to auxotrophs, and the like. Examples of bacterial selectable markers are the dal genes from Bacillus subtilis or Bacillus licheniformis, or markers which confer antibiotic resistance such as ampicillin, kanamycin, erythromycin, chloramphenicol or tetracycline resistance. Furthermore, selection may be accomplished by co-transformation, e.g., as described in WO 91/09129, where the selectable marker is on a separate vector.

The procedures used to ligate the elements described above to construct the recombinant expression vectors of the present invention are well known to one skilled in the art (see, e.g., Sambrook et al., 1989, supra).

The transformation of the Bacillus cell may, for instance, be effected by protoplast transformation (see, e.g., Chang and Cohen, 1979, Molecular General Genetics 168: 111–115), by using competent cells (see, e.g., Young and Spizizin, 1961, Journal of Bacteriology 81: 823–829, or Dubnau and Davidoff-Abelson, 1971, Journal of Molecular Biology 56: 209–221), by electroporation (see, e.g., Shigekawa and Dower, 1988, Biotechniques 6: 742–751), or by conjugation (see, e.g., Koehler and Thorne, 1987, Journal of Bacteriology 169: 5271–15 5278).

The present invention is further described by the following examples which should not be construed as limiting the scope of the invention.

EXAMPLES

All primers and oligos were synthesized on an Applied Biosystems Model 394 Synthesizer (Applied Biosystems, Inc., Foster City, Calif.) according to the manufacturer's instructions.

Example 1

Construction of Bacillus subtilis Donor Sstrain BW154

Several genes (spoIIAC, aprE, nprE, amyE, and srfC) were deleted in the Bacillus subtilis A164 (ATCC 6051A) and 1630 (NCFB 736) host strains described herein. In order to accomplish this task, plasmids containing deleted versions of these genes were introduced into these strains using the pLS20-mediated conjugation system (Koehler and Thorne, 1987, supra). Briefly, this system is comprised of a Bacillus subtilis "donor" strain which contains a large plasmid designated pLS20. pLS20 encodes the functions necessary for mobilizing pLS20 into a "recipient" strain of Bacillus subtilis. In addition, it has been shown that plasmids such as pUB110 and pBC16 are also mobilized by this conjugation system (in the presence of pLS20). These plasmids contain a cis-acting region (oriT) and a gene (orf-beta) encoding a trans-acting function that acts at the oriT site and facilitates the mobilization of these plasmids into a recipient strain. Plasmids containing only oriT can also be mobilized if the donor strain contains both pLS20 and either pUB110 or pBC16 (in this case, orf-beta function is provided in trans).

The pLS20 plasmid or a derivative such as pXO503 (Koehler and Thorne, 1987, supra) must be present in order for a strain to be a proficient donor. In addition, it is also desirable to have a means of counter-selecting against the donor strain after the conjugation has been completed. A counter-selection scheme has been developed that is very "clean" (no background) and easy to implement. This involves introducing a deletion in the dal gene of the donor strain (encodes the D-alanine racemase enzyme which is required for cell wall synthesis) and selecting against the donor strain by growing the cell mixture from a conjugation experiment on solid media devoid of D-alanine (this amino acid must be added exogenously to the media in order for a dal- strain of Bacillus subtilis to grow).

In order to delete the genes mentioned above, pE194 replicons (erythromycin resistance) (Gryczan et al., 1982, Journal of Bacteriology 152: 722–735) containing deleted versions of the genes and the oriT sequence had to be mobilized into the Bacillus subtilis A164 and A1630 strains. A suitable donor strain should have the following characteristics: 1) a deletion in the dal gene (for counter-selection) and 2) it must also contain pLS20 (pXO503 would be unsuitable in this case since the pE194 replicons must be maintained by erythromycin selection and pXO503 already confers resistance to this antibiotic) and either pUB110 or pBC16 to supply orf-beta function in trans. A description of how Bacillus subtilis BW154 was constructed as a donor strain follows.

(A) Introduction of a dal Deletion in Bacillus subtilis to Yield Bacillus subtilis BW96.

First, a strain of Bacillus subtilis with a mutation in the bac-1 gene (this mutation abolishes the ability of the strain to synthesize the dipeptide antibiotic bacilysin) was chosen because it has been shown previously that wild-type Bacillus subtilis cells actually kill other species of Bacillus during the conjugation process and this killing potential is greatly reduced in cells which are bac-1. Therefore, all donor strains have been constructed in a bac-1 background.

The first step in constructing a suitable donor strain was to delete a portion of the dal gene in the Bacillus subtilis strain 1A758 which is bac-1 (Bacillus Stock Center, Columbus, Ohio). A deleted version of the dal gene was constructed in vitro which could be exchanged for the wild-type dal gene on the bacterial chromosome. The 5' and 3' portions of the dal gene were PCR-amplified using primers 1 and 2 to amplify the 5' portion of the gene (nucleotides 19–419, the A of the ATG codon is +1) and primers 3 and 4 to amplify the 3' portion of the gene (nucleotides 618–1037).

Primer 1: 5'-GAGCTCACAGAGATACGTGGGC-3' (SEQ ID NO:1)

Primer 2: 5'-GGATCCACACCAAGTCTGTTCAT-3' (SEQ ID NO:2) (BamHI site underlined)

Primer 3: 5'-GGATCCGCTGGACTCCGGCTG-3' (SEQ ID NO:3) (BamHI site underlined)

Primer 4: 5'-AAGCTTATCTCATCCATGGAAA-3' (SEQ ID NO:4) (HindIII site underlined)

The amplification reactions (100 μl) contained the following components: 200 ng of Bacillus subtilis 168 chromosomal DNA, 0.5 μM of each primer, 200 μM each of dATP, dCTP, dGTP, and dTTP, 1× Taq polymerase buffer, and 1 U of Taq DNA polymerase. Bacillus subtilis 168 chromosomal DNA was obtained according to the procedure of Pitcher et al., 1989, Letters in Applied Microbiology 8: 151–156. The reactions were performed under the following conditions: 95° C. for 3 minutes, then 30 cycles each at 95° C. for 1 minute, 50° C. for 1 minute, and 72° C. for 1 minute, followed by 5 minutes at 72° C. Reactions products were analyzed by agarose gel electrophoresis. Both the 5' and 3' PCR products were cloned into the pCRII vector of the TA Cloning Kit (Invitrogen, San Diego, Calif.). according to the manufacturer's instructions. A pCRII clone was identified which contained the 5' half of the dal gene in an orientation such that the BamHI site introduced by the PCR primer was adjacent to the BamHI site of the pCRII polylinker (the other orientation would place the BamHI sites much farther apart). The pCRII clone containing the 3' half of the dal gene was then digested with BamHI and HindIII and the dal gene fragment was then cloned into the BamHI-HindIII site of the aforementioned pCRII clone containing the 5' half of the dal gene which generated a pCRII vector containing the dal gene with a ~200 bp deletion in the middle flanked by a NotI site at the 5' end (part of the pCRII polylinker) and a HindIII site at the 3' end of the gene.

In order to introduce this dal deletion into the bacterial chromosome, the deleted gene was cloned into the temperature-sensitive Bacillus subtilis replicon pE194 (Gryczan et al., 1982, supra). The deleted dal gene was then introduced into the chromosome in two steps: first by integrating the plasmid via homologous recombination into the chromosomal dal locus, followed by the subsequent removal of the plasmid (again via homologous recombination), leaving behind the deleted version of the dal gene on the bacterial chromosome. This was accomplished as follows: the deleted dal gene fragment (described above) was cloned into the NotI-HindIII site of the temperature sensitive plasmid pSK$^+$/pE194 (essentially replacing the pSK$^+$ vector sequences with the dalΔ fragment). Plasmid pSK$^+$/pE194 was constructed as follows: both Bluescript SK$^+$ (Stratagene, La Jolla, Calif.) and pE194 were digested with XbaI. The pSK$^+$ vector was then treated with calf intestinal alkaline phosphatase and the two plasmids were ligated together. The ligation mix was used to transform the E. coli strain DH5α and transformants were selected on LB plates containing ampicillin (100 μg/ml) and X-ga1. Plasmid was purified from several "white" colonies and a chimera comprised of both pE194 and pSK$^+$ was identified by restriction enzyme digestion followed by gel electrophoresis. This plasmid was digested with HindIII and NotI. The fragment comprising the pE194 replicon was then gel-purified and ligated with gel-purified dalΔ gene fragment (HindIII-NotI). The ligation mix was used to transform the bac-1 strain Bacillus subtilis 1A758 (Bacillus Stock Center, Columbus, Ohio), and transformants were selected on Tryptone blood agar base (TBAB) plus erythromycin (5 μg/ml) plates and grown at the permissive temperature of 34° C. Plasmid DNA was purified from five erythromycin resistant transformants and analyzed by restriction enzyme digestion/gel electrophoresis. A plasmid was identified which corresponded to pE194 containing the dal-deleted fragment. The strain harboring this plasmid was subsequently used for the introduction of the dal deletion into the chromosome via homologous recombination.

In order to obtain the first cross-over (integration of the dal deletion plasmid into the dal gene on the chromosome), the transformed strain was streaked onto a TBAB plate containing D-alanine (0.1 mg/ml) and erythromycin (5 μg/ml) and grown overnight at the non-permissive temperature of 45° C. A large colony was restreaked under the same conditions yielding a homogeneous population of cells containing the temperature-sensitive plasmid integrated into the dal gene on the chromosome. At the non-permissive temperature, only cells which contain the plasmid in the chromosome were capable of growing on erythromycin since the plasmid was incapable of replicating. In order to obtain the second cross-over event (resulting in excision of the plasmid from the chromosome leaving behind the deleted version of the dal gene), a loopful of cells was transferred to 20 ml of Luria broth supplemented with D-alanine (0.1 mg/ml) and grown to late log phase without selection at the permissive temperature of 34° C. to permit function of the origin of replication and occurrence of the second cross-over event. Cells were transferred 4 times more (1/100 dilution each transfer) to allow the plasmid to excise from the chromosome and segregate out of the population. Finally, cells were plated for single colonies at 34° C. on TBAB plates supplemented with D-alanine (0.1 mg/ml) and replica-plated onto TBAB plates without D-alanine (0.1 mg/ml) and TBAB plates with D-alanine (0.1 mg/ml) and erythromycin (5 μg/ml) to score colonies which were dal- and erm$^s$. Two out of 50 colonies yielded this phenotype. The resulting strain was designated *Bacillus subtilis* BW96, a bac-1, dal- strain. (B) Introduction of pLS20 and pBC16 into the bac-1, dal-deleted *Bacillus subtilis* strain to yield the conjugation proficient donor strain *Bacillus subtilis* BW154.

A donor strain was chosen for introducing plasmids pLS20 and pBC16 into *Bacillus subtilis* BW96 wherein the donor strain should have the following characteristics: basically an erythromycin sensitive *Bacillus subtilis* strain (in order to provide a counter-selection against the donor strain) which contains both pLS20 and pBC16. A dal-deleted *Bacillus subtilis* strain containing pLS20 and pBC16 was chosen as a suitable donor strain which was constructed as follows: *Bacillus subtilis* DN1686 (U.S. Pat. No. 4,920,048) was transformed with pHV1248 (Petit et al., 1990, *Journal of Bacteriology* 172: 6736–6740) to make cells erythromycin resistant. The conjugative element pLS20 was transferred to the *Bacillus subtilis* DN1686 (pHV1248) strain along with pBC16 by conjugation with *Bacillus subtilis* (natto) 3335 UM8 (Koehler and Thorne, 1987, supra). The transconjugants were selected as tetracycline and erythromycin resistant colonies possessing a dal deletion. Colonies carrying pLS20 were scored by their ability to transfer pBC16 to other *Bacillus subtilis* strains by conjugation. Finally the conjugative strain was cured of pHV1248 by raising the temperature to 50° C. yielding the donor strain: *Bacillus subtilis* DN1686 containing pLS20 and pBC16.

In order to introduce these plasmids into *Bacillus subtilis* BW96, a suitable counter-selection scheme had to be implemented, and therefore, *Bacillus subtilis* BW96 was transformed with a temperature-sensitive plasmid pSK$^+$/pE194 conferring erythromycin resistance which could be subsequently removed by growth at a non-permissive temperature. The pLS20 and pBC16 plasmids were mobilized from *Bacillus subtilis* DN1686 containing pLS20 and pBC16 into *Bacillus subtilis* BW96 (harboring pSK$^+$/pE194) according to the following procedure. A loopful of each cell type was mixed together on a TBAB plate supplemented with D-alanine (50 μg/ml) and incubated at 33° C. for 5 hours. The cells were scraped from the plate and transferred to 1 ml of LB medium. The cells were spread at various dilutions onto TBAB plates supplemented with tetracycline (10 μg/ml), erythromycin (5 μg/ml), and D-alanine (50 μg/ml) and grown at 34° C. to select for recipient cells which acquire pBC16 and in many cases pLS20 as well. To test whether pLS20 was also present in any of the transconjugants, ten colonies were tested for their ability to transfer pBC16 into *Bacillus subtilis* PL1801.

*Bacillus subtilis* PL1801 is *Bacillus subtilis* 168 (Bacillus Stock Center, Columbus, Ohio) with deletions of the genes apr and npr). However, *Bacillus subtilis* 168 may also be used. Donors capable of mobilizing pBC16 must contain pLS20 as well. Once a conjugation proficient strain was identified (*Bacillus subtilis* bac-1, dal- containing pLS20 plus pBC16 plus pSK$^+$/pE194), the pSK$^+$/pE194 plasmid was cured from the strain by propagating the cells in LB medium supplemented with tetracycline (5 μg/ml) and D-alanine (50 μg/ml) overnight at 45° C., plating for single colonies at 33° C. on TBAB plates supplemented with D-alanine (50 μg/ml), and identifying erythromycin sensitive colonies. This procedure yielded *Bacillus subtilis* BW154 which is *Bacillus subtilis* bac-1, dal- containing pLS20 and pBC16.

A summary of the Bacillus strains and plasmids is present in Table I.

TABLE I

| Bacterial strains and plasmids | |
|---|---|
| *Bacillus subtilis* strains: | |
| *B. subtilis* (natto) | pLS20 |
| DN1686 | dal- |
| DN1280 | dal- |
| MT101 | DN1280 (pXO503) |
| 1A758 | 168 bac-1 (Bacillus Stock Center, Columbus, Ohio) |
| BW96 | 1A758 dalΔ |
| BW97 | 1A758 dalΔ::cat (pXO503) |
| BW99 | 1A758 dalΔ (pPL2541-tet) |
| BW100 | 1A758 dalΔ (pXO503), (pPL2541-tet) |
| PL1801 | aprA, nprA |
| Plasmids: | |
| pBC16 | Mob$^+$, Tc$^r$ |
| pE194 | temperature sensitive |
| pLS20 | Tra$^+$ |
| pXO503 | Tra$^+$, MLS$^r$ (=pLS20::Tn917) |
| pPL2541-tet | Mob$^+$, Tc$^r$ (pE194 ts ori) |
| pCAsub2 | Mob$^+$, Cm$^r$, Ap$^r$, (pE194 ts ori) |
| pSK$^+$/pE194 | Em$^r$, Ap$^r$, temperature-sensitive |
| pShv2 | Tra$^+$, Em$^r$, Cm$^r$, temperature-sensitive |
| pHV1248 | Em$^r$, temperature-sensitive |

Tra$^+$ implies that the plasmid confers upon any *Bacillus subilis* strain bearing it the ability to conjugate, that is, the plasmid encodes all of the functions for mobilizing a conjugatable plasmid from the donor to a recipient cell.

Mob$^+$ implies that a plasmid is capable of being mobilized via conjugation by a strain which contains a Tra$^+$ plasmid (pLS20 or pXO503). The plasmid must contain a cis-acting sequence and a gene encoding a trans-acting protein (oriT and orf-beta, respectively, in the case of pBC16) or just an oriT sequence (in the case of pPL254-tet, here a plasmid supplying orf-beta function in trans such as pBC16 must also be present in the cell as well).

Example 2

Deletion of the spoIIAC Gene of *Bacillus subtilis* A164 (ATCC 6051A)

A deleted version of the spoIIAC gene which encodes sigma F permitting cells to proceed through stage II of sporulation was created by splicing by overlap extension (SOE) technique (Horton et al., 1989, *Gene* 77: 61–68). *Bacillus subtilis* A164 (ATCC 6051A) chromosomal DNA was obtained by the method of Pitcher et al., 1989, supra. Primers 5 and 6 shown below were synthesized for PCR amplification of a region from *Bacillus subtilis* A164 chromosomal DNA extending from 205 nucleotides upstream of the ATG start codon of the spoIIAC gene to 209 nucleotides downstream of the ATG start. The underlined nucleotides of the upstream primer were added to create a HindIII site. The underlined nucleotides of the downstream primer are complementary to bases 507 to 524 downstream of the ATG translational start codon. Primers 7 and 8 were synthesized to PCR-amplify a region extending from 507 to 884 nucleotides downstream of the ATG translational start codon. The underlined region of primer 7 is exactly complementary to the 3' half of primer 6 used to amplify the upstream fragment.

Primer 5: 5'-AAGCTTAGGCATTACAGATC-3' (SEQ ID NO:5)

Primer 6: 5'-CGGATCTCCGTCATTTTCCAGCCCGAT GCA GCC-3' (SEQ ID NO:6)

Primer 7: 5'-GGCTGCATCGGGCTGGAAAATGAC GGAGATCCG-3' (SEQ ID NO:7)

Primer 8: 5'-GATCACATCTTTCGGTGG-3' (SEQ ID NO:8)

The two sets of primers were used to amplify the upstream and downstream spoIIAC fragments in separate PCR amplifications. The amplification reactions (25 μl) contained the following components: 200 ng of Bacillus subtilis A164 chromosomal DNA, 0.5 μM of each primer, 200 μM each of dATP, dCTP, dGTP, and dTTP, 1×Taq polymerase buffer, and 0.625 U of Taq DNA polymerase. The reactions were performed under the following conditions: 96° C. for 3 minutes, then 30 cycles each at 96° C. for 1 minute, 50° C. for 1 minute, and 72° C. for 1 minute, followed by 3 minutes at 72° C. to insure addition of a terminal adenine residue to the amplified fragments (Invitrogen, San Diego, Calif.). Amplification of the expected products was verified by electrophoresis through a 1.5% agarose gel.

A new PCR mixture containing 2.5 μl of each amplification reaction above was then performed under the same conditions but containing only primers 5 and 8, producing a "spliced" fragment of 1089 nucleotides, representing the spoIIAC gene lacking 298 internal nucleotides. This fragment was cloned into the pCRII vector using the Invitrogen TA Cloning Kit according to the manufacturer's instructions, excised as a HindIII-EcoRI fragment, and then cloned into HindIII/EcoRI-digested pShv2. pShv2 is a shuttle vector constructed by ligating XbaI-cut pBCSK⁺ (Stratagene, La Jolla, Calif.) containing oriT of pUB110 with XbaI-cut pE194 (FIG. 1), followed by ligation of oriT from pUB110 as a PCR-amplified fragment containing SstI compatible ends. The oriT fragment permits mobilization of the plasmid into Bacillus subtilis A164 by pLS20-mediated conjugation (Battisti et al., 1985, Journal of Bacteriology 162: 543–550). pShv2-ΔspoIIAC was transformed into donor strain Bacillus subtilis BW154 (Example 1). Bacillus subtilis BW154 (pShv2-ΔspoIIAC) was used as a donor strain to introduce the shuttle vector containing the deleted gene into Bacillus subtilis A164.

Exchange of the deleted gene with the intact chromosomal gene was effected by conjugation of Bacillus subtilis BW154 transformed with pShv2-ΔspoIIAC with Bacillus subtilis A164, selection of erythromycin-resistant transconjugants, and growth at 45° C. At this temperature, the pE194 replicon is inactive, and cells are only able to maintain erythromycin resistance by Campbell integration of the plasmid containing the deleted gene at the spoIIAC locus. A second recombination event, resulting in loopout of vector DNA and replacement of the intact spoIIAC gene with the deleted gene, was effected by growth of the strain for two rounds in LB medium without antibiotic selection at 34° C., a temperature permissive for function of the pE194 replicon. Colonies in which gene replacement had occurred were selected according to the following criteria: 1) absence of erythromycin (erm) resistance encoded by the shuttle vector pShv2, 2) decreased opacity on sporulation medium, indicating failure to sporulate, and 3) PCR amplification with primers 5 and 8 to obtain a fragment of 791 nucleotides instead of 1089 nucleotides representing the undeleted version of the gene.

Example 3

Deletion of the nprE Gene of Bacillus subtilis A164 ΔspoIIAC

An upstream portion of the neutral protease (nprE) gene (nucleotides 40–610 downstream of the GTG start codon) was PCR-amplified from Bacillus subtilis A164 ΔspoIIAC chromosomal DNA prepared in the manner described in Example 2 using primers 9 and 10 shown below. A downstream portion of the nprE gene (nucleotides 1040–1560) was PCR amplified using primers 11 and 12 shown below. Primers 10 and 11 were designed such that there would be a 15 base pair overlap between the two fragments (denoted by underlining). The amplification reactions (25 μl) contained the same components and were performed under the same conditions specified in Example 2.

Primer 9: 5'-CGTTTATGAGTTTATCAATC-3' (SEQ ID NO:9)

Primer 10: 5'-AGACTTCCCAGTTTGCAGGT-3' (SEQ ID NO:10)

Primer 11: 5'-CAAACTGGGAAGTCTCGACGG TTCATTCTTCTCTC-3' (SEQ ID NO:11)

Primer 12: 5'-TCCAACAGCATTCCAGGCTG-3' (SEQ ID NO:12)

The amplified upstream and downstream fragments were gel purified with the Qiaex II Kit according to the manufacturer's instructions (Qiagen, Chatsworth, Calif.). A new PCR mixture (100 μl) containing approximately 20 ng of each purified fragment was performed. The SOE reaction was performed under the following conditions: cycles 1–3 in the absence of primers to generate a "spliced" fragment, and cycles 4–30 in the presence of primers 9 and 12 under the conditions specified in Example 2. The amplified SOE fragment was cloned into the pCRII vector and verified by restriction analysis. The fragment was then cloned into pShv2 as a BamHI-XhoI fragment. This plasmid, pShv2-ΔnprE, was transformed into Bacillus subtilis BW154 to generate a suitable donor strain for conjugation. The plasmid was then mobilized into Bacillus subtilis A164 ΔspoIIAC. The ΔnprE gene was introduced into the chromosome of Bacillus subtilis A164 ΔspoIIAC by temperature shift as described in Example 2. An nprE- phenotype was scored by patching erm$^s$ colonies onto TBAB agar plates supplemented with 1% non-fat dry milk and incubating overnight at 37° C. (An nprE- strain had a noticeably reduced clearing zone.) The 430 base pair deletion was verified by PCR analysis on chromosomal DNA using primers 9 and 12.

Example 4

Deletion of the aprE Gene of Bacillus subtilis A164 ΔspoIIAC ΔnprE

SOE was used to create a deleted version of the Bacillus subtilis aprE gene which encodes an alkaline subtilisin protease. An upstream portion of aprE was PCR amplified using primers 13 and 14 shown below from *Bacillus subtilis* A164 chromosomal DNA prepared as described in Example 2 to create a fragment extending from 189 nucleotides upstream of the translational start codon to 328 nucleotides downstream of the start. The underlined nucleotides of primer 13 were included to add an EcoRI site. The underlined nucleotides of primer 14 were added to provide complementarity to the downstream PCR fragment and to add a SalI site. A downstream portion of the aprE gene was PCR-amplified using primers 15 and 16 to create a fragment extending from 789 nucleotides to 1306 nucleotides downstream of the aprE translational start codon. Underlined regions of primers 14 and 15 were added to provide complementarity between the upstream and downstream fragments. The underlined nucleotides of primer 16 were included to add a HindIII site. The amplification reactions (25 µl) contained the same components and were conducted under the same conditions as described in Example 2.

Primer 13: 5'-GC<u>GAATTC</u>TACCTAAATAGAGATA AAATC-3' (SEQ ID NO:13)

Primer 14: 5'-<u>GTTTACCGCACCTACGTCGAC</u>CCT GTGTAGCCTTGA-3' (SEQ ID NO:14)

Primer 15: 5'-<u>TCAAGGCTACACAGGGTCGAC</u> GTAGGTGCGGTA AC-3' (SEQ ID NO:15)

Primer 16: 5'-GC<u>AAGCTT</u>GACAGAGAACAGAGAA GCCAG-3' (SEQ ID NO:16)

The amplified upstream and downstream fragments were purified using the Qiaquick PCR Purification Kit according to the manufacturer's instructions (Qiagen, Chatsworth, Calif.). The two purified fragments were then spliced together using primers 13 and 16. The amplification reaction (50 µl) contained the same components as above except the chromosomal DNA was replaced with 2 µl each of the upstream and downstream PCR products. The reactions were incubated for 1 cycle at 96° C. for 3 minutes (without the dNTPs and Taq polymerase), and then for 30 cycles each at 96° C. for 1 minute and 72° C. for 1 minute. This resulted in a deleted version of aprE lacking 460 nucleotides from the coding region. The reaction product was isolated by agarose electrophoresis, cloned into pCRII, excised as an EcoRI-HindIII fragment, and then cloned into EcoRI/HindIII-digested pShv2 to yield pShv2-ΔaprE. This plasmid was introduced into the donor strain described above for conjugal transfer into *Bacillus subtilis* A164 ΔspoIIAC ΔnprE.

Replacement of aprE with the deleted gene was effected as described above for spoIIAC and nprE. Colonies in which aprE had been deleted were selected by erythromycin sensitivity and reduced clearing zones on agar plates with an overlay containing 1% non-fat dry milk. Deletion of aprE was confirmed by PCR.

*Bacillus subtilis* A164 ΔspoIIAC ΔnprE ΔaprE is herein designated *Bacillus subtilis* A164 Δ3.

Example 5

Deletion of the amyE gene of *Bacillus subtilis* A164 ΔspoIIAC ΔnprE ΔaprE

SOE was used to create a deleted version of the amyE gene which encodes *Bacillus subtilis* alpha-amylase. An upstream portion of amyE was PCR-amplified from *Bacillus subtilis* A164 chromosomal DNA using primers 17 and 18 shown below. This created a fragment extending from 421 nucleotides upstream of the amyE translational start codon to nucleotide 77 of the amyE coding sequence, adding a SalI site at the upstream end and SfiI and NotI sites at the downstream end. A downstream portion of amyE was PCR-amplified using primers 19 and 20 shown below. This created a fragment extending from nucleotide 445 to nucleotide 953 of the amyE coding sequence, and added SfiI and NotI sites at the upstream end and a HindIII site at the downstream end. Restriction sites are denoted by underlining. The amplification reactions (25 µl) contained the same components and were conducted under the same conditions as described in Example 2.

The two fragments were then spliced together by PCR using primers 17 and 20. The amplification reaction (25 µl) contained the same components as above except the chromosomal DNA was replaced with 2 µl each of the upstream and downstream PCR products. The reactions were incubated for 1 cycle at 96° C. for 3 minutes (without the dNTPs and Taq polymerase), and then at 96° C. for 1 minute and 72° C. for 1 minute for 30 cycles. This reaction fused the two fragments by overlap at the region of complementarity between the two (the SfiI and NotI sites) and resulted in a fragment of amyE lacking 367 nucleotides from the coding region and having an SfiI site and a NotI site incorporated between the two portions of amyE. The reaction product was isolated by electrophoresis using a 1% agarose gel according to standard methods. This fragment was cloned into pCRII according to the manufacturer's instructions to yield pCRII-ΔamyE.

Primer 17: 5'-C<u>GTCGAC</u>GCCTTTGCGGTAGTGGT GCTT-3' (SEQ ID NO: 17) (SalI site underlined)

Primer 18: 5'-C<u>GCGGCCGC</u>AGG<u>CCCTTAAGGCC</u>AG AACCAAATGAA-3' (SEQ ID NO:18) (NotI and SfiI sites underlined)

Primer 19: 5'-T<u>GGCCTTAAGGGCC</u>T<u>GCGGCCGC</u>G ATTTCCAATG-3' (SEQ ID NO: 19) (SfiI and NotI sites underlined)

Primer 20: 5'-G<u>AAGCTT</u>CTTCATCATCATTGGCA TACG-3' (SEQ ID NO:20) (HindIII site underlined)

pShv2.1 was created by digesting pShv2 with NotI, filling in the cohesive ends with Klenow fragment and dNTPs, and religating the plasmid. This procedure destroyed the NotI recognition site of pShv2. The deleted amyE fragment was excised from pCRII-ΔamyE as a SalI-HindIII fragment and cloned into SalI/HindIII-digested pShv2.1 to yield pShv2.1-ΔamyE. This plasmid was introduced into *Bacillus subtilis* BW154 for conjugal transfer into *Bacillus subtilis* A164 ΔspoIIAC ΔnprE ΔaprE.

Replacement of amyE with the deleted gene was effected as described above for spoIIAC, nprE, and aprE. Colonies in which gene replacement had occurred were selected by erythromycin sensitivity and the inability to produce a zone of clearing on starch azure overlay plates. Deletion of amyE was confirmed by PCR amplification of the deleted gene from chromosomal DNA using primers 17 and 20.

Example 6

Deletion of the srfC gene of *Bacillus subtilis* A164 ΔspoIIAC Δnpr Δapr ΔamyE to produce *Bacillus subtilis* A164 ΔspoIIAC ΔnprE ΔaprE ΔamyE ΔsrfC Primers 21–24 shown below were synthesized for the creation of a deletion in srfC of the surfactin operon. Primer 21 overlaps an existing HindIII site (underlined) in the srfC gene, and in conjunction with primer 22 permits PCR amplification of a region extending from 410 nucleotides to 848 nucleotides downstream of the translational start of srfC. The underlined portion of primer 22 is complementary to nucleotides 1709–1725 downstream of the ATG start codon. Primers 23 and 24 permit PCR amplification of a region of 1709 to 2212 nucleotides downstream of the translational start of srfC. The underlined portion of primer 23 is complementary to nucleotides 835–848 downstream of the ATG codon. The amplification reactions (25 µl) contained the same components and were performed under the same conditions as described in Example 2.

Primer 21: 5'-<u>AAGCTT</u>TGAATGGGTGTGG-3' (SEQ ID NO:21)

Primer 22: 5'-<u>CCGCTTGTTCTTTCAT</u>CCCCTGAA ACA ACTGTACCG-3' (SEQ ID NO:22)

Primer 23: 5'-<u>CAGTTGTTTCAGGGG</u>ATGAAAGAA CAAGCGGCTG-3' (SEQ ID NO:23)

Primer 24: 5'-CTGACATGAGGCACTGAC-3' (SEQ ID NO:24)

Primers and other contaminants were removed from the PCR products with a Qiagen PCR spin column (Qiagen, Chatsworth, Calif.). The complementarity between the two PCR-generated fragments permitted splicing by SOE. The PCR products (2 µl or approximately 50 ng each) were spliced together under the same PCR conditions as described above with the "outside primers", primers 21 and 24, except that the first 3 cycles were performed before addition of the primers to extend the overlapping regions. The SOE reaction resulted in a 955 nucleotide fragment that lacked an internal 859 nucleotides of the srfC gene. The deleted portion represents the region of srfC responsible for addition of the seventh amino acid leucine to the surfactin molecule, and furthermore results in a frameshift mutation which results in termination of the peptide prior to the thioesterase active site-like region, presumed to be involved in surfactin release from the SrfC protein (Cosmina et al., 1993, supra).

Replacement of srfC with the deleted gene was effected as described above for spoIIAC, nprE, and aprE, and amyE. Colonies in which gene replacement had occurred were selected by erythromycin sensitivity, the inability to produce a zone of clearing on blood agar plates (Grossman et al., 1993, *Journal of Bacteriology* 175: 6203–6211), and lack of foaming upon cultivation for 4 days at 37° C. and 250 rpm in 250 ml shake flasks containing 50 ml of PS-1 medium composed of 10% sucrose, 4% soybean flour, 0.42% anhydrous disodium phosphate, and 0.5% calcium carbonate supplemented with 5 µg of chloramphenicol per ml. Deletion of srfC was confirmed by PCR amplification of the deleted gene from chromosomal DNA using primers 21 and 24.

*Bacillus subtilis* A164 ΔspoIIAC ΔnprE ΔaprE ΔamyE ΔsrfC is herein designated *Bacillus subtilis* A164 Δ5.

Example 7

Construction of *Bacillus subtilis* A1630 ΔspoIIAC ΔnprE ΔaprE ΔamyE ΔsrfC

*Bacillus subtilis* A1630 ΔspoIIAC ΔnprE ΔaprE ΔamyE ΔsrfC was constructed from *Bacillus subtilis* A1630 (NCFB 736, formerly NCDO 736) according to the same procedures described in Examples 1–6 for *Bacillus subtilis* A164 ΔspoIIAC ΔnprE ΔaprE ΔamyE ΔsrfC (*Bacillus subtilis* A164 Δ5), using the deletion plasmids constructed for the *Bacillus subtilis* A164 deletions.

*Bacillus subtilis* A1630 ΔspoIIAC Δnpr Δapr ΔamyE ΔsrfC is herein designated *Bacillus subtilis* A1630 Δ5.

Example 8.

Construction of a vector for integration of an amyQ promoter-amyM transcriptional cassette into *Bacillus subtilis*Δ164 strains.

A transcriptional fusion was constructed which placed NOVAMYL™ (amyM) gene and its native ribosome binding site immediately downstream of the promoter of the amyQ gene which encodes a *Bacillus amyloliquefaciens* amylase (BAN™, Novo Nordisk A/S, Bagsvaerd, Denmark). The amyQ promoter (BAN™ promoter) was PCR-amplified using primers 25 and 26 listed below and the same conditions as described in Example 2 above, cloned into the pCRII vector, sequenced to verify error-free amplification, and then ligated into the multiple cloning site of the *E. coli-Bacillus subtilis* shuttle vector pHP13-ampMCS that had been cut with Sfi I and Sst I.

Primer25: 5'-TTT<u>GGCCTTAAGGGCC</u>TGCA<u>ATCGAT</u> TGTTTGAGAAAAGAAG-3' (SfiI and ClaI sites underlined, respectively) (SEQ ID NO:25)

Primer26:5'-TTT<u>GAGCTC</u>CATTTTCTTATACAAATT ATATTTTACATATCAG-3' (SstI site underlined) (SEQ ID NO:26)

pHP13-ampMCS, a variant of pHP13 (Haima et al., 1987, Molecular and General Genetics 209: 335–342), was constructed by cutting pUC9 with AatII, blunting with Klenow fragment and deoxyribonucleotides, then cutting with HindIII. The larger 2.2 kb fragment was gel-purified with a Qiaex kit (Qiagen, Thousand Oaks, Calif.). pHP13 was cut with HpaI (which cuts within the erythromycin resistance gene), blunted, and then cut with HindIII. The larger 3.0 kb fragment released from pHP13 was then ligated to the 2.1 kb pUC9 fragment containing the pUC9 origin of replication and ampicillin resistance gene. Finally, the pUC9 MCS was replaced with a new MCS created by annealing 100 pmol each of the following two oligonucleotides 27 and 28 in 50 mM NaCl, 10 mM Tris pH 7.5, and 1 mM EDTA, boiling for 5 min, and cooling slowly to room temperature over a 2 hour time period.

Oligo27 :5'-AGCTAGGCCTTAAGGGCCCGG GACGTCGAGCTCAAGCTTGCGGCCGCCA TGGTCGACG-3' (SEQ ID NO:27)

Oligo 28: 5'-AATTCGTCGACCATGGCGGCC GCAAGCTTGAGCTCGACGTCCCGGGCCCT TAAGGCC-3' (SEQ ID NO:28)

Figure 2:
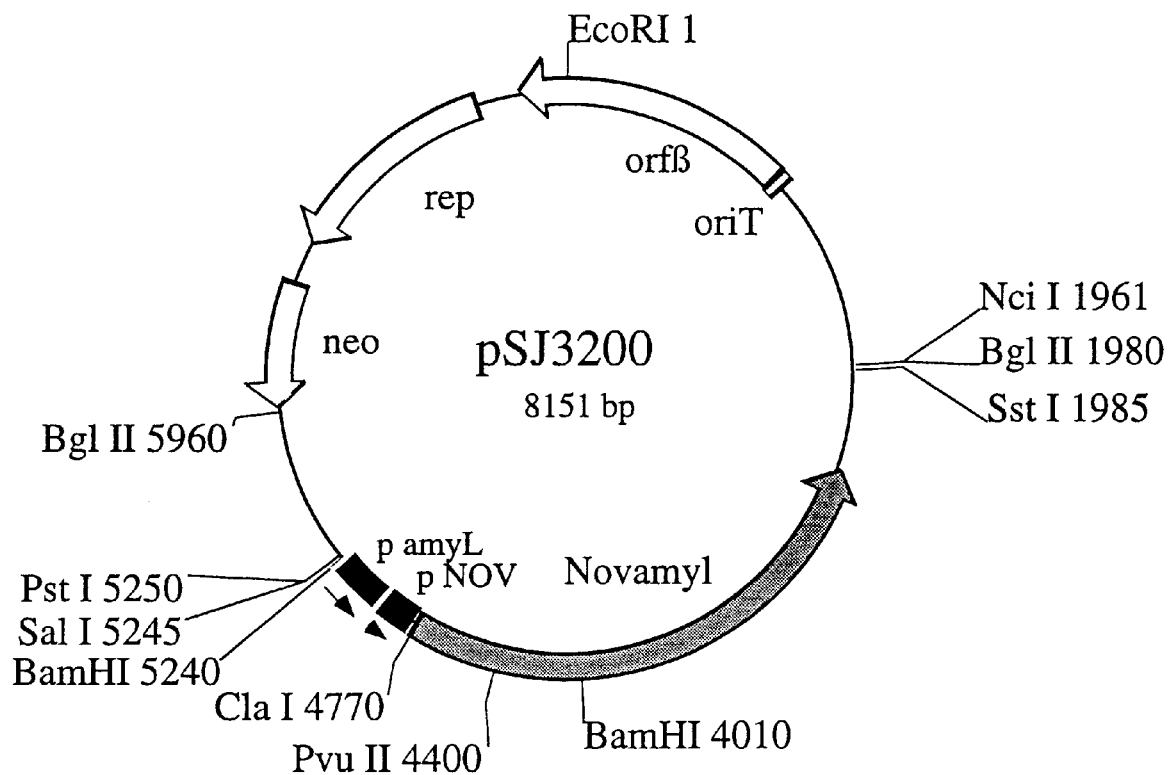
FIG. 2 shows a restriction map of pSJ3200.

Since the primers used to PCR-amplify the BAN™ (amyQ) promoter introduced SfiI and SstI sites, it was necessary to place an SstI site upstream of the NOVAMYL™ (amyM) open reading frame in order to construct the transcriptional fusion. Therefore, a 5' PCR primer (primer 27 listed below) containing an SstI linker was designed to anneal 4 nucleotides upstream of the NOVAMYL™ (amyM) ribosome binding site. This PCR primer lies immediately downstream, and therefore omits from amplification, a potential stem structure. A PCR primer (primer 28 listed below) overlapping a PvuII site was used in conjunction with the SstI-containing primer to amplify, under the conditions described in Example 2 and using 200 ng of pSJ3200 (FIG. 2) as template DNA, a 327 nucleotide fragment encoding the N-terminus of NOVAMYL™.

Primer 29: 5'-CT<u>GAGCTC</u>TACGAAAGGAGACACA CATGC-3' (SstI site underlined) (SEQ ID NO:29) Primer 30: 5'-ACGCC<u>CAGCTG</u>TTTAAGATAAG-3' (PvuII site underlined) (SEQ ID NO:30)

Figure 3:
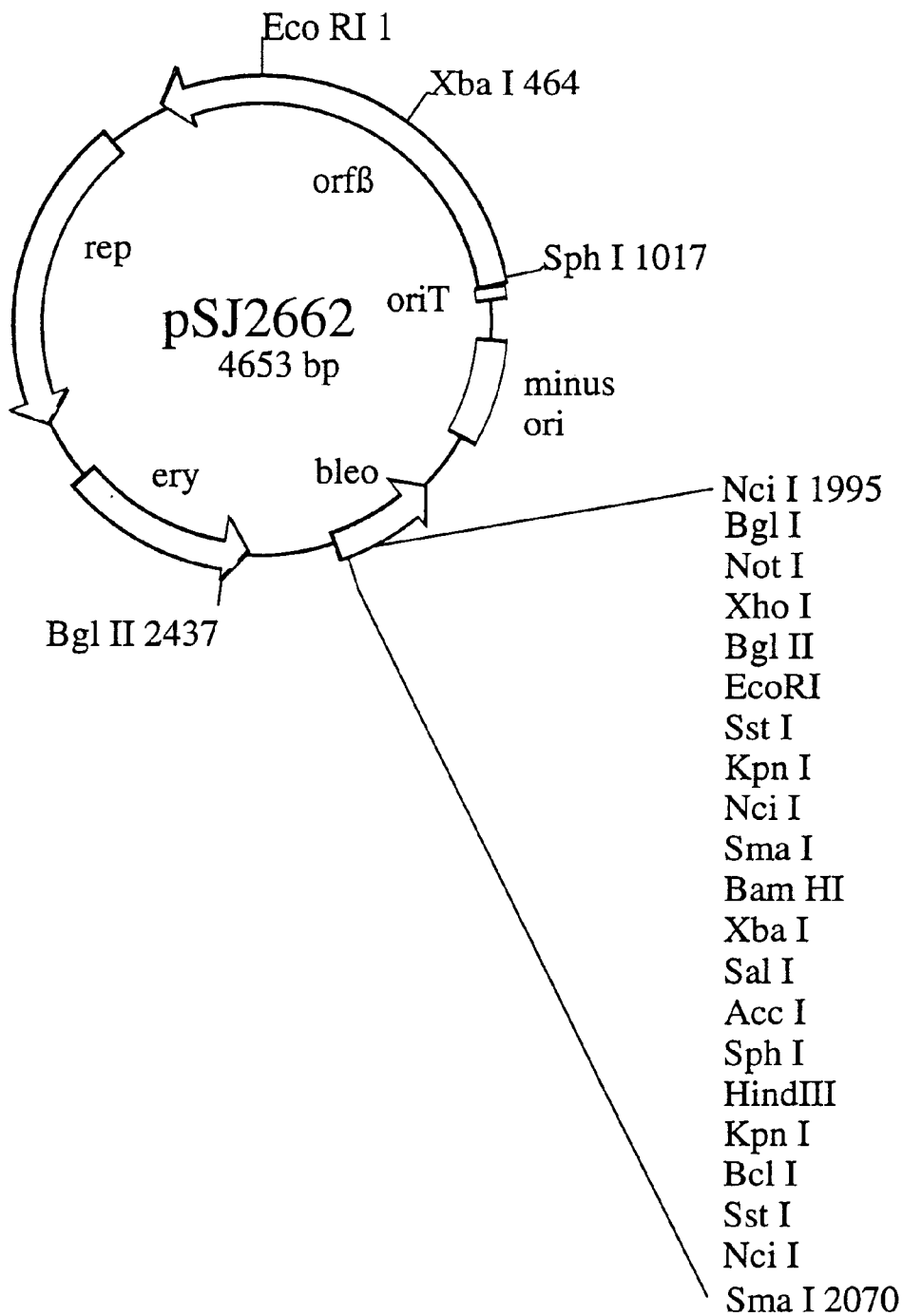
FIG. 3 shows a restriction map of pSJ2662.

Plasmid pSJ3200 (FIG. 2) was constructed by cloning the NOVAMYL™ gene as a PstI-BglII fragment into pSJ2662 (FIG. 3), a derivative of pUB110 containing a larger MCS.

To reconstruct the amyM gene, the 327 nucleotide PCR-amplified fragment was excised as an SstI-PvuII fragment, and cloned together with the downstream 2.2 kb PvuII-SstI fragment (encoding the latter portion of amyM) in a 3-way ligation into SstI-cut pUC118.

Figure 4:
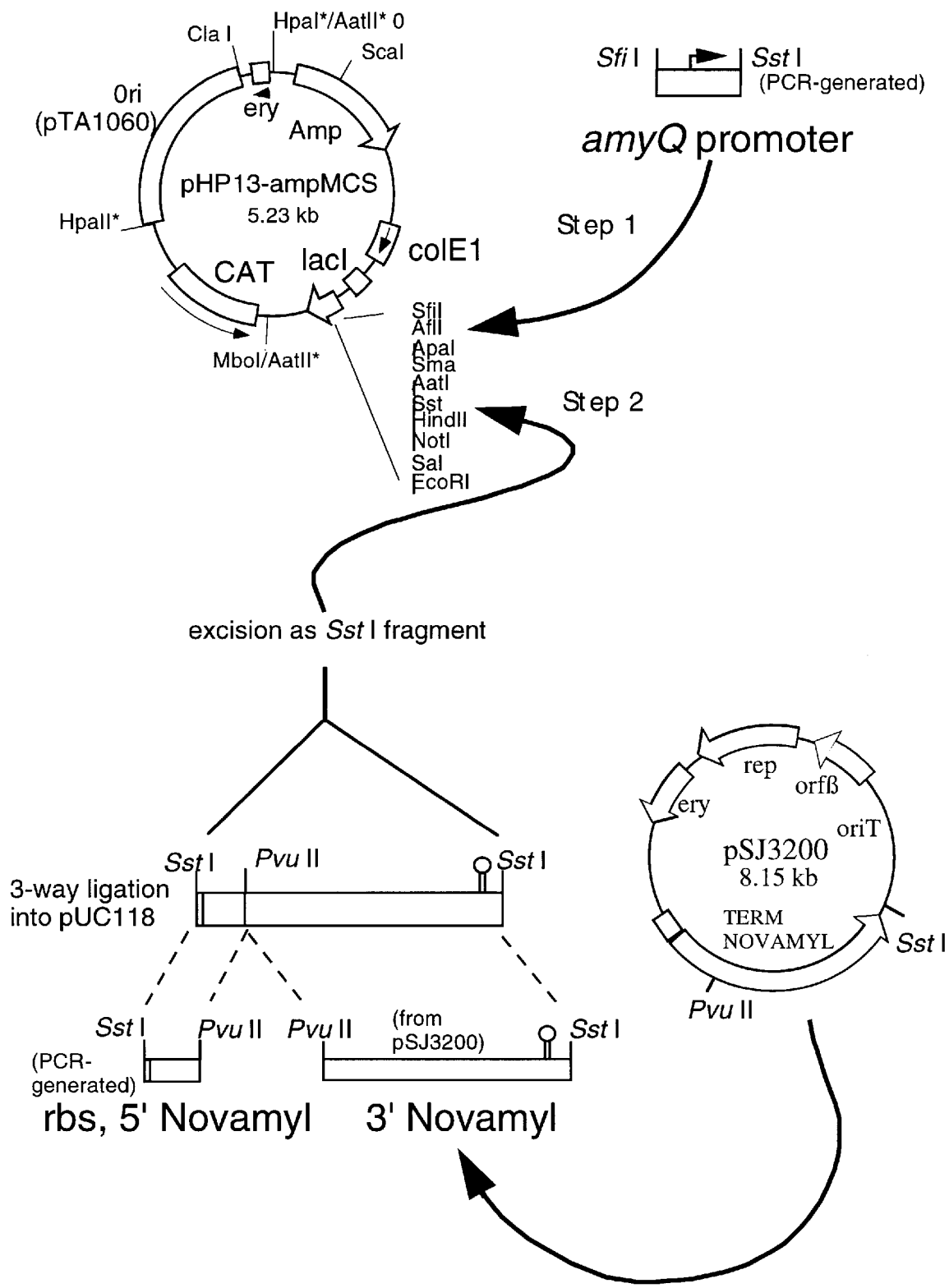
FIG. 4 shows the construction of the amyQ promoter-amyM gene fusion in pSJ2882-MCS.

The reconstructed amyM gene was then removed as a SstI fragment and cloned downstream of the amyQ promoter contained in pSJ2882-MCS. FIG. 4 summarizes these cloning steps. pSJ2882-MCS is derived from pHP13 (Haima et al., 1987, *Molecular General Genetics* 209: 335–342), but contains a SfiI-NotI-flanked MCS, and also a SstI 0.5 kb fragment containing the oriT region from pUB110. This latter fragment permits mobilization of the plasmid into *Bacillus subtilis*Δ164 by pLS20-mediated conjugation (Battisti et al., 1985, *Journal of Bacteriology* 162: 543–550).

Ligation reactions were transformed directly into *Bacillus subtilis* PL1801 spoIIE. Proper orientation of the amyM open reading frame relative to the amyQ promoter in pSJ2882-MCS was determined by the presence or absence of a halo surrounding colonies growing on starch-azure plates containing 5 μg chloramphenicol per ml.

Figure 5:
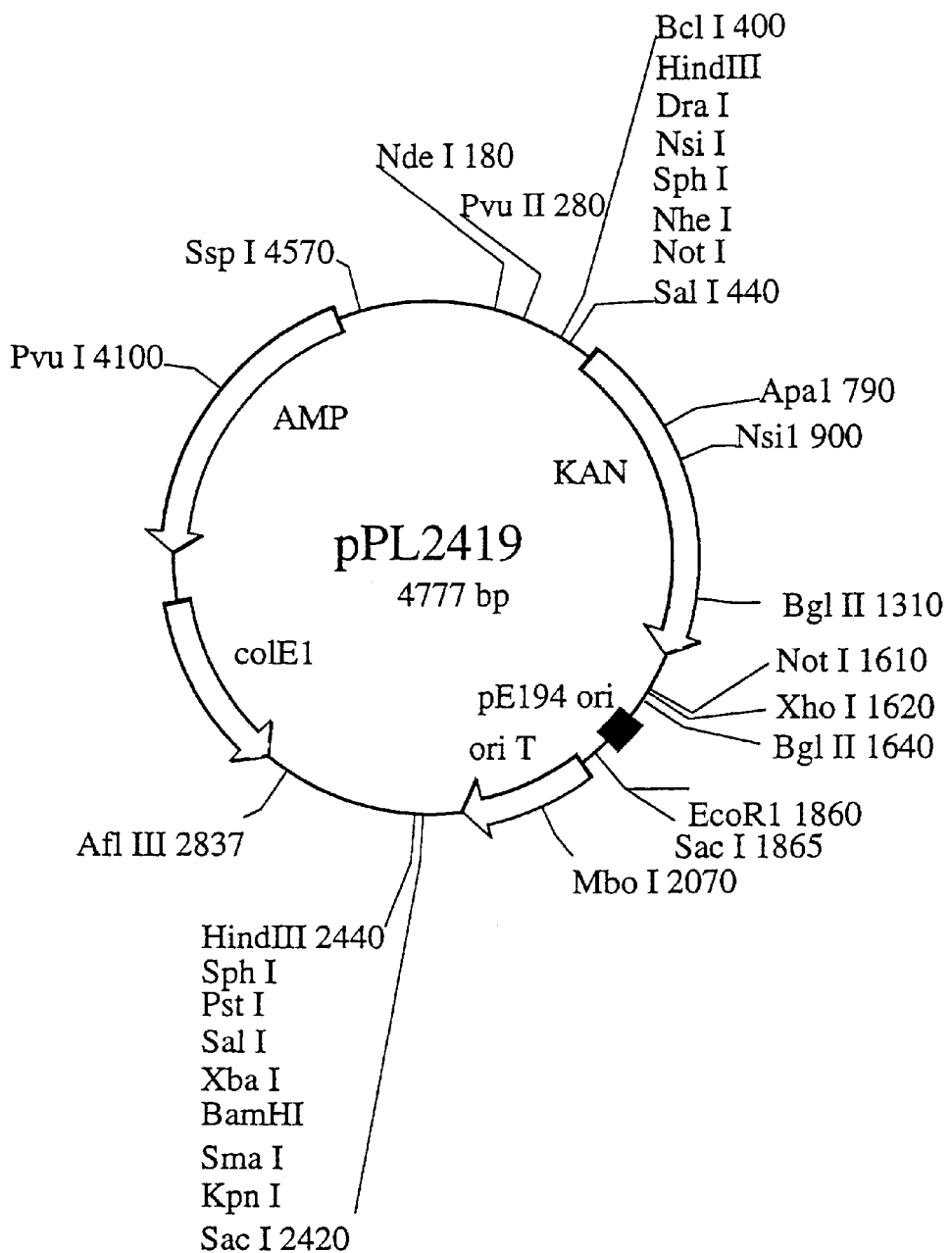
FIG. 5 shows a restriction map of pPL2419.

To construct the integration vector pCAsub2, the neomycin resistance gene of pPL2419 (FIG. 5) was excised by digestion with BclI and BglII and replaced with the chloramphenicol acetyltransferase (cat) gene-containing BamHI fragment from pMI1101 (Youngman et al., 1984, *Plasmid* 12: 1–9) to create plasmid pPL2419-cat. (BamHI sticky ends are compatible with BclI and BglII sticky ends.) Then, the multiple cloning site (MCS) of pPL2419-cat was replaced with a new MCS containing SfiI and NotI sites created by annealing the two oligonucleotides together shown below (SEQ ID NO:31 and SEQ ID NO:32) by mixing 100 pmol of each oligo in 50 mM NaCl, 10 mM Tris pH 7.5, 1 mM EDTA, boiling for 5 minutes, and cooling slowly to room temperature over 2 hours. 5'-<u>AGCTT</u> GGCCTTAAGGGCCCGATATCGGATCCGCGGCCGCT G<u>CAGGTAC</u>-3' (HindIII and KpnI compatible sites are underlined, SfiI and NotI sites are double-underlined) (SEQ ID NO:31) 5'-CTGCAG CGGCCGCGGATCCGA TATCGGGCCCTTAAGGCCA-3' (SEQ ID NO:32)

Figure 6:
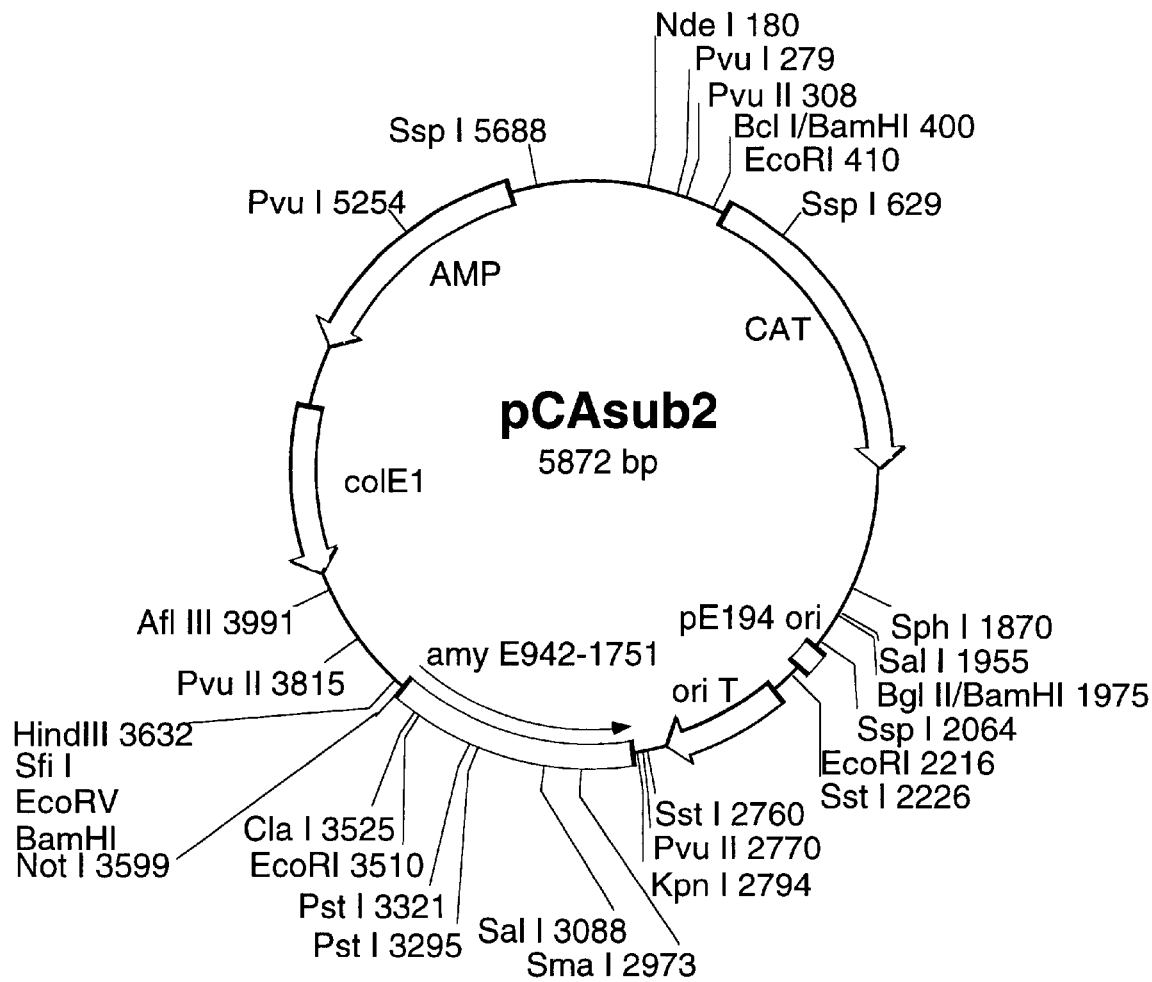
FIG. 6 shows a restriction map of pCAsub2.

The annealed oligonucleotides (2 μl) were ligated to HindIII and KpnI-cut pPL2419-cat (0.2 μg) to generate p2419MCS5-cat. Then, nucleotides 942 to 1751 of amyE (GenBank Locus BSAMYL, accession numbers V00101, J01547) were PCR-amplified as described in Example 2 using primers depicted below containing NotI and KpnI (Asp718) linkers (SEQ ID NO:33 and SEQ ID NO:34) and *Bacillus subtilis* strain A164 Δ5 chromosomal DNA (prepared as described in Example 2) as template, and inserted into NotI and Asp718-digested p2419MCS5, generating integration vector pCAsub2 (FIG. 6), CAsub referring to chloramphenicol resistance, amylase homology, for use in a *subtilis* host.

5'-<u>GCGGCCGC</u>GATTTCCAATGAG-3' (nucleotides added to create NotI site are underlined) (SEQ ID NO:33)
5'-<u>GGTACC</u>TGCATTTGCCAGCAC-3' (nucleotides added to create Asp 718I site are underlined) (SEQ ID NO:34)

Integration of this vector alone into *Bacillus subtilis* 168 and plating on starch azure overlay plates showed complete elimination of amylase activity.

Figure 7:
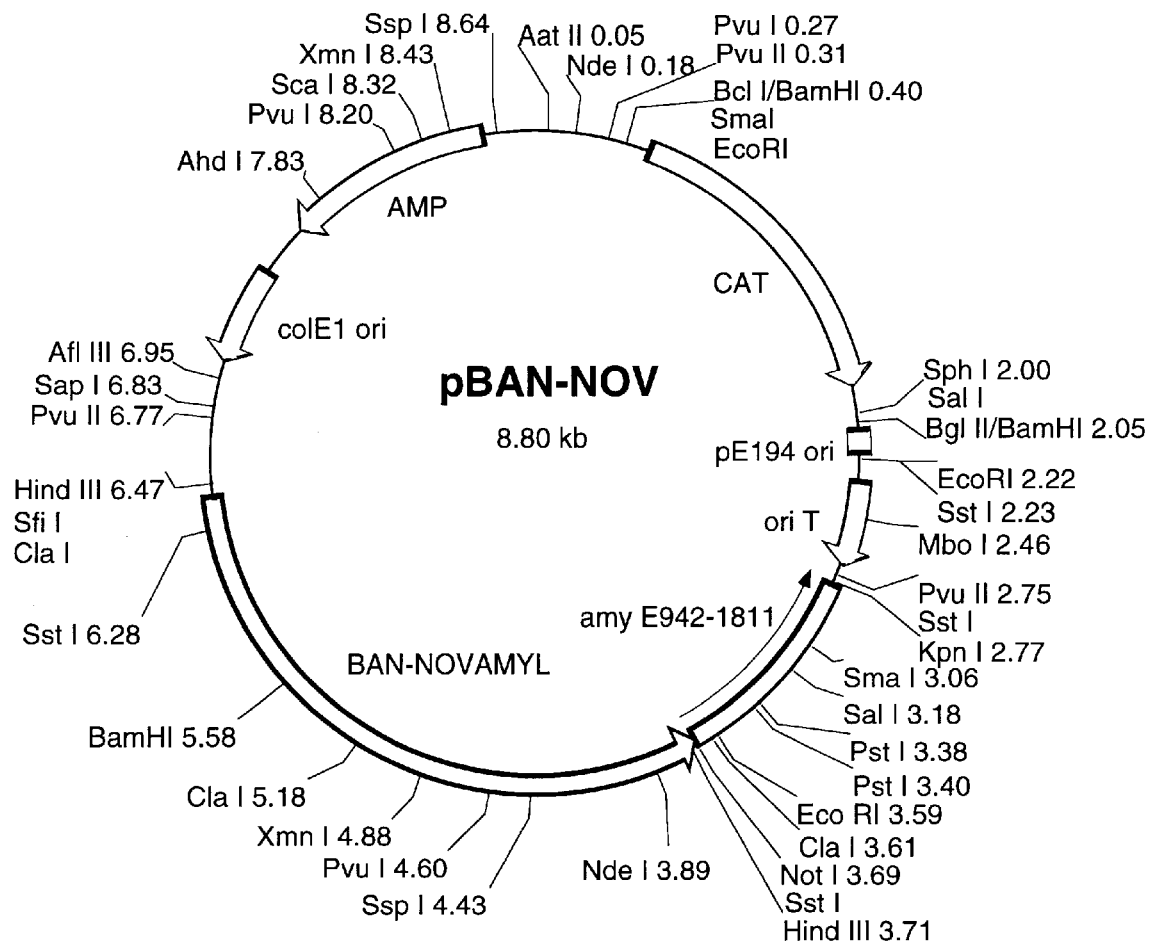
FIG. 7 shows a restriction map of pBAN-NOV.

The amyQ promoter-amyM construction was removed from pSJ2882-MCS as an SfiI-NotI cassette and cloned into pCAsub2 cut with the same enzymes to generate a complete integration vector pBAN-NOV (FIG. 7).

Example 9

Construction of *Bacillus subtilis* donor strain BW100

Figure 8:
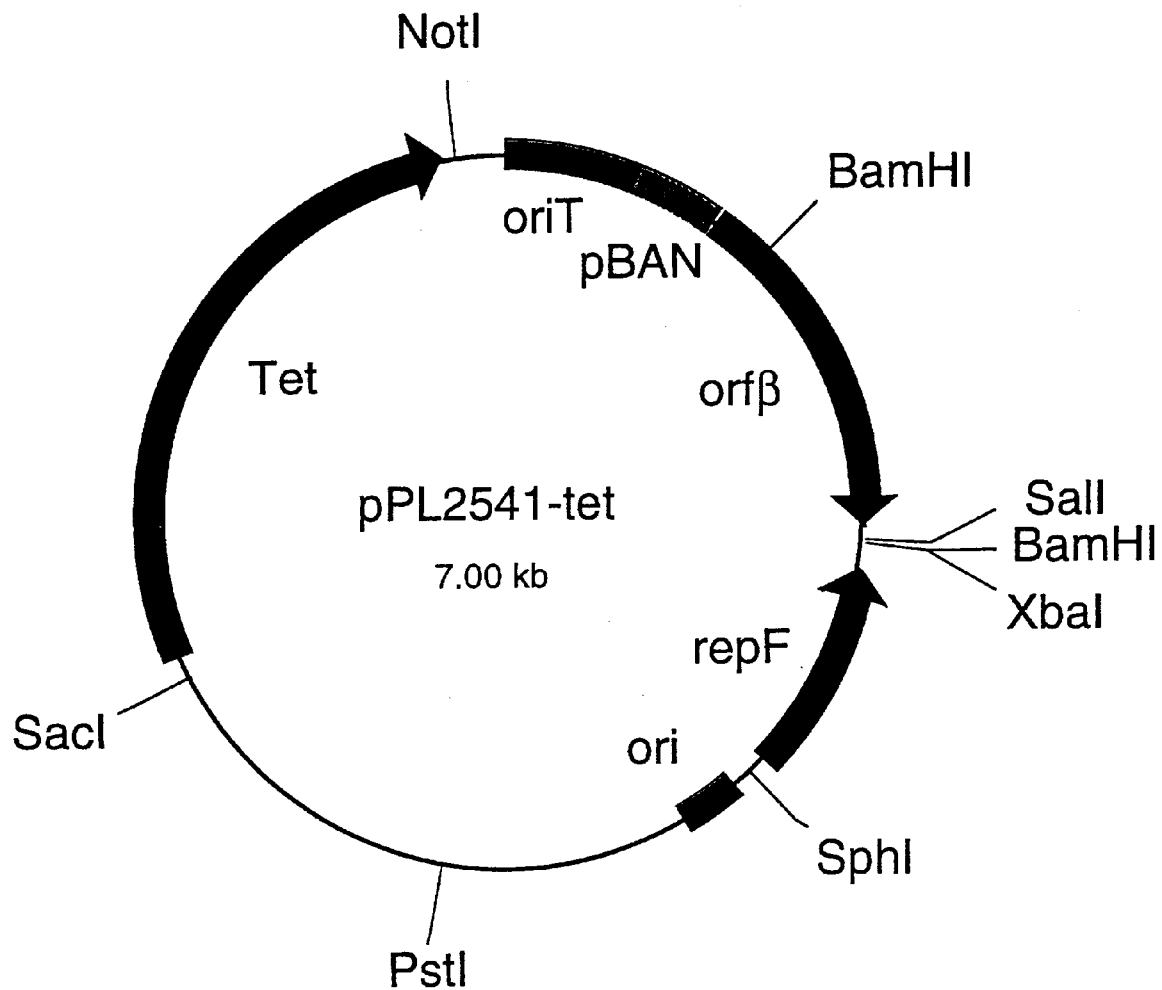
FIG. 8 shows a restriction map of pPL2541-tet.

A suitable donor strain was constructed which was capable of maintaining and mobilizing a pE194-based "slave" integration plasmid such as pCAsub2 (conferring chloramphenicol resistance and containing oriT) described in Example 8. Such a donor strain should have the following characteristics: bac-1-, dal-deleted, containing pLS20 or pXO503 and a pE194-based "helper" plasmid (containing both oriT and orf-beta for mobilizing both the "helper" and "slave" and also repF, for providing repF protein in trans to enable the "slave" plasmid to replicate and be maintained as a plasmid replicon) (WO 91/09129). The strain was constructed as follows: *Bacillus subtilis* BW96 was transformed with the helper plasmid pPL2541-tet (FIG. 8), which provides a counter-selection against a donor strain, to produce *Bacillus subtilis* BW99. Next, plasmid pXO503 was introduced into *Bacillus subtilis* BW99 via conjugation, utilizing *Bacillus subtilis* BW97 as a donor strain. *Bacillus subtilis* BW97 was constructed as follows: first the pXO503 plasmid was mobilized from *Bacillus subtilis* MT101 donor strain into the bac-1 strain *Bacillus subtilis* 1A758, and selecting for transconjugants on TBAB plus eythromycin (5 μg/ml) plates (the dal- donor will not grow since D-alanine is not contained in the media). This yielded a bac-1- strain of *Bacillus subtilis* harboring the pXO503 plasmid. *Bacillus subtilis* MT101 is derived from *Bacillus subtilis* DN1280, which is a derivative of *Bacillus subtilis* 168 containing a deletion in the dal gene (Diderichsen, In A. T. Ganesan and J. A. Hoch, editors, *Bacillus Molecular Genetics and Biotechnology Applications*, Academic Press, Inc., New York, 1986).

Next, the cat gene cassette (conferring chloramphenicol resistance) flanked by BamHI sites described in Example 8 was inserted into the BamHI site of the pCRII-dalΔ plasmid. This plasmid was linearized with ScaI and transformed into the bac-1 strain containing the conjugation plasmid pXO503, selecting for chloramphenicol resistance (via double cross-over homologous recombination) on TBAB plus D-alanine (0.1 mg/ml) plus chloramphenicol (5 μg/ml) which yielded *Bacillus subtilis* BW97, a bac-1, dalΔ::cat conjugation proficient donor strain. Finally, *Bacillus subtilis* BW97 was conjugated with *Bacillus subtilis* BW99 containing pPL2541-tet, selecting for transconjugants on TBAB plates plus D-alanine (0.1 mg/ml) plus tetracycline (10 μg/ml) plus erythromycin (5 μg/ml) yielding the donor strain *Bacillus subtilis* BW100: a bac-1, dal-deleted, *Bacillus subtilis* strain containing pXO503 and helper plasmid pPL2541-tet.

Example 10

Integration and amplification of the amyQ promoter-amyM cassette in *Bacillus subtilis*Δ164 strains The *Bacillus subtilis* BW100 donor strain described in Example 9 containing the amyQ promoter-amyM cassette in pBAN-NOV as well as the helper plasmid pPL2541-tet was conjugated by pLS20-mediated conjugation (Battisti et al., 1985, supra) with the *Bacillus subtilis* A164 Δ3 and *Bacillus subtilis*Δ164 Δ5 strains.

*Bacillus subtilis*Δ164 Δ3 and Δ5 transconjugants were then grown in 125 ml shake flasks containing 10 ml of LB broth supplemented with 5 μg chloramphenicol per ml at 45° C. for two successive passages, and then plated at 45° C. to block replication of the pPL2541-tet helper plasmid and to select for integration of the integrative plasmid at the amyE locus. Integrants were then plated at successively higher chloramphenicol concentrations of 15, 30, 45, 60, and 80 μg of chloramphenicol per ml to select for amplification of the chloramphenicol-containing amyQ promoter-amyM cassette.

Example 11

Shake flask cultivation of *Bacillus subtilis*Δ164 strains transformed with the amyQ promoter-amyM cassette

*Bacillus subtilis*Δ164 Δ3 and *Bacillus subtilis*Δ164 Δ5, containing chromosomally integrated copies of the amyQ promoter-amyM cassette or the integration vector alone, were cultivated for 4 days at 37° C. and 250 rpm in 250 ml shake flasks containing 50 ml of PS-1 medium.

Culture supernatants were sampled at approximately 50 and 100 hours, treated with 2 mM PMSF final concentration, and frozen. To estimate NOVAMYL™ expression, supernatants were mixed with an equal volume of 2X Laemmli loading buffer, immediately boiled, and loaded on 14% or 8–16% acrylamide TRIS-glycine gels purchased from a commercial source (NOVEX, San Diego, Calif.). Known amounts of a NOVAMYL™ standard were also loaded on the same gel to estimate the amount of NOVAMYL™ produced. In some cases, NOVAMYL™ titer was determined using maltotriose as substrate. Specifically, a sample of the enzyme is incubated with maltotriose at pH 5.0 and 37° C. for 30 minutes. The reaction is then stopped by adjusting the pH to approximately 11. The amount of glucose produced from the breakdown of maltotriose to glucose and maltose is then measured with glucose dehydrogenase and NADH at 340 nm under standard conditions.

Known amounts of a NOVAMYL™ standard (Novo Nordisk A/S, Bagsvaerd, Denmark) are also run.

The results showed that the strain not deleted in srfC had an 8 cm head of foam compared to a 0.5 cm head of foam for the srfC-deleted strain after 2 days of cultivation. The lack of production of surfactin by the srfC-deleted strain was confirmed by the lack of hemolysis on blood agar plates. The results further indicated that both strains produced similar amounts of NOVAMYL™, but the srfC-deleted strain exhibited a marked reduction of foaming compared to the non-deleted strain.

Example 12

Fermentation of *Bacillus subtilis*Δ164 Strains

*Bacillus subtilis*Δ164 Δ3 and *Bacillus subtilis*Δ164 Δ5, integrated/amplified and integrated/amplified with the slave plasmid pCAsub2 alone, were each cultivated in a 3 liter fermentor containing 1.5 liters of medium composed of typical carbon and nitrogen sources as well as mineral salts, trace elements and at least 3 ml of antifoam (Sigma mixed Type 289, Sigma Chemical Company, St. Louis, Mo.) per liter of medium. The cultures were sparged with air at 1.5 liters per minute and agitated with two standard rushton turbines at 1000 to 1500 rpm. The fermentations were maintained at a temperature between 37° C. and 39° C.

The amount of foaming was quantitatively assessed by measuring the volume of liquid carried out of the fermentor by the action of foaming. NOVAMYL™ activity was measured as described in Example 11.

The results indicated that *Bacillus subtilis*Δ164 Δ3 began to produce foam within 5 hours of the fermentation where the foam filled the 1.5 liter head space of the fermentor and began to overflow through the exhaust lines into a graduated catch flask. Within 10 to 20 hours between 700 to 900 ml of liquid volume were typically lost from the fermentor by foaming over. After this period, the system stabilized, but only 45% to 60% of the original volume remained in the fermentor making the strain unsuitable for large-scale production. Similar fermentations with *Bacillus subtilis*Δ164 Δ5 did not experience any volume loss due to foaming during at least 50 hours of fermentation. The amount of NOVAMYL™ produced per ml was similar with both strains.

---

What is claimed is:

1. A method for producing a polypeptide, comprising:

(a) cultivating a mutant of a corresponding parent Bacillus cell under conditions conducive for the production of the polypeptide, wherein (i) the mutant cell comprises a first nucleic acid sequence encoding the polypeptide and a second nucleic acid sequence comprising a modification of at least one of the genes responsible for the production of a surfactin or isoform thereof selected from the group consisting of a srfA, srfB, srfC, srfD, and sfp gene, and (ii) the mutant cell produces less of the surfactin or isoform thereof than the parent Bacillus cell when cultured under the same conditions; and (b) isolating the polypeptide from the cultivation medium.

2. The method of claim 1, wherein the Bacillus cell is a *Bacillus alkalophilus, Bacillus amyloliquefaciens, Bacillus brevis, Bacillus circulans, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* cell.

3. The method of claim 2, wherein the Bacillus cell is a *Bacillus subtilis* cell.

4. The method of claim 3, wherein the polypeptide is heterologous to the *Bacillus subtilis* cell.

5. The method of claim 3, wherein the *Bacillus subtilis* cell is *Bacillus subtilis* ATCC 6051 or *Bacillus subtilis* ATCC 6051 A.

6. The method of claim 5, wherein the polypeptide is heterologous to *Bacillus subtilis* ATCC 6051 or *Bacillus subtilis* ATCC 6051 A.

7. The method of claim 3, wherein the *Bacillus subtilis* cell is *Bacillus subtilis* NCFB 736.

8. The method of claim 7, wherein the polypeptide is heterologous to *Bacillus subtilis* NCFB 736.

9. The method of claim 2, wherein the Bacillus cell is a *Bacillus amyloliquefaciens* cell.

10. The method of claim 9, wherein the polypeptide is heterologous to the *Bacillus amyloliquefaciens* cell.

11. The method of claim 2, wherein the Bacillus cell is a *Bacillus lentus* cell.

12. The method of claim 1, wherein the polypeptide is heterologous to the *Bacillus lentus* cell.

13. The method of claim 2, wherein the Bacillus cell is a *Bacillus licheniformis* cell.

14. The method of claim 1, wherein the polypeptide is heterologous to the *Bacillus licheniformis* cell.

15. The method of claim 1, wherein the gene is srfA.

16. The method of claim 1, wherein the gene is srfB.

17. The method of claim 1, wherein the gene is srfC.

18. The method of claim 1, wherein the gene is srfD.

19. The method of claim 1, wherein the gene is sfp.

20. The method of claim 1, wherein the mutant cell produces at least about 25% less of the surfactin or isoform thereof than the parent Bacillus cell when cultured under identical conditions.

21. The method of claim 1, wherein the modification results in the production of a non-foaming variant of the surfactin or isoform thereof.

22. The method of claim 1, wherein the polypeptide is heterologous to the Bacillus cell.

23. The method of claim 1, wherein the mutant cell further comprises a modification of one or more genes which encode a protease.

24. The method of claim 23, wherein the genes are nprE and/or aprE.

25. The method of claim 1, wherein the mutant cell further comprises a modificaton of the spoIIAC and/or amyE genes.

26. A mutant of a corresponding parent Bacillus cell, comprising at least two copies of a first nucleic acid sequence encoding a heterologous polypeptide and a second nucleic acid sequence comprising a modification of at least one of the genes responsible for the production of a surfactin or isoform thereof selected from the group consisting of a SrfA, srfB, srfC, srfD, and sfp gene, wherein the mutant cell produces less of the surfactin or isoform thereof than the parent Bacillus cell when cultured under the same conditions.

27. A mutant of a corresponding parent Bacillus cell, comprising at least two copies of a first nucleic acid sequence encoding a native polypeptide and a second nucleic acid sequence comprising a modification of at least one of the genes responsible for the production of a surfactin or isoform thereof selected from the group consisting of a srfA, srfB, srfC, srfD, and sfp gene, wherein the mutant cell produces less of the surfactin or isoform thereof than the parent Bacillus cell when cultured under the same conditions.

28. A method for obtaining the mutant of claim 26, comprising:

(a) introducing into the Bacillus cell a first nucleic acid sequence comprising a modification of at least one of the genes responsible for the production of a surfactin or isoform thereof selected from the group consisting of a srfA, srfB, srfC, srfD, and sfp gene, and a second nucleic sequence encoding a polypeptide which is heterologous to the Bacillus cell; and (b) identifying the mutant cell from step (a) comprising the nucleic acid sequences, wherein the mutant cell produces less of the surfactin or isoform thereof than the parent Bacillus cell when cultured under the same conditions.

29. A method of obtaining the mutant of claim 27, comprising:

(a) introducing into the Bacillus cell a first nucleic acid sequence comprising a modification of at least one of the genes responsible for the production of a surfactin or isoform thereof selected from the group consisting of a srfA, srfB, srfC, srfD, and sfp gene, and a second nucleic sequence encoding a polypeptide which is native to the Bacillus cell; and (b) identifying the mutant from step (a) comprising the nucleic acid sequences, wherein the mutant cell produces less of the surfactin or isoform thereof than the parent Bacillus cell when cultured under the same conditions.

* * * * *

UNITED STATES PATENT AND TRADEMARK OFFICE
CERTIFICATE OF CORRECTION

PATENT NO. : 5,958,728
DATED      : September 28, 1999
INVENTOR(S): Sloma et al.

It is certified that error appears in the above-identified patent and that said Letters Patent is hereby corrected as shown below:

Title page, item [73] delete "Novo NordiskBiotech" and insert –Novo Nordisk Biotech–
Col. 37, Line 24, delete "SrfA" and insert –srfA–

Signed and Sealed this

Sixth Day of June, 2000

Attest:

Q. TODD DICKINSON

*Attesting Officer*    *Director of Patents and Trademarks*

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (xi) SEQUENCE DESCRIPTION: SEQ ID NO:1:

GAGCTCACAG AGATACGTGG GC                                     22

(2) INFORMATION FOR SEQ ID NO:2:

(i) SEQUENCE CHARACTERISTICS:

(A) LENGTH: 23 base pairs
           (B) TYPE: nucleic acid
           (C) STRANDEDNESS: single
           (D) TOPOLOGY: linear (xi) SEQUENCE DESCRIPTION: SEQ ID NO:2:

GGATCCACAC CAAGTCTGTT CAT                                              23

(2) INFORMATION FOR SEQ ID NO:3:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (xi) SEQUENCE DESCRIPTION: SEQ ID NO:3:

GGATCCGCTG GACTCCGGCT G                                                21

(2) INFORMATION FOR SEQ ID NO:4:

(i) SEQUENCE CHARACTERISTICS:
           (A) LENGTH: 22 base pairs
           (B) TYPE: nucleic acid
           (C) STRANDEDNESS: single
           (D) TOPOLOGY: linear (xi) SEQUENCE DESCRIPTION: SEQ ID NO:4:

AAGCTTATCT CATCCATGGA AA                                               22

(2) INFORMATION FOR SEQ ID NO:5:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:5:

AAGCTTAGGC ATTACAGATC                                                  20

(2) INFORMATION FOR SEQ ID NO:6:

(i) SEQUENCE CHARACTERISTICS:
           (A) LENGTH: 33 base pairs
           (B) TYPE: nucleic acid
           (C) STRANDEDNESS: single
           (D) TOPOLOGY: linear (xi) SEQUENCE DESCRIPTION: SEQ ID NO:6:

CGGATCTCCG TCATTTTCCA GCCCGATGCA GCC                                   33

(2) INFORMATION FOR SEQ ID NO:7:

(i) SEQUENCE CHARACTERISTICS:
           (A) LENGTH: 33 base pairs
           (B) TYPE: nucleic acid
           (C) STRANDEDNESS: single
           (D) TOPOLOGY: linear (xi) SEQUENCE DESCRIPTION: SEQ ID NO:7:

GGCTGCATCG GGCTGGAAAA TGACGGAGAT CCG                                   33

(2) INFORMATION FOR SEQ ID NO:8:

(i) SEQUENCE CHARACTERISTICS:
           (A) LENGTH: 18 base pairs
           (B) TYPE: nucleic acid (C) STRANDEDNESS: single
        (D) TOPOLOGY: linear (xi) SEQUENCE DESCRIPTION: SEQ ID NO:8:

GATCACATCT TTCGGTGG                                                         18

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

CGTTTATGAG TTTATCAATC                                                       20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:10:

AGACTTCCCA GTTTGCAGGT                                                       20

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:11:

CAAACTGGGA AGTCTCGACG GTTCATTCTT CTCTC                                      35

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:12:

TCCAACAGCA TTCCAGGCTG                                                       20

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:13:

GCGAATTCTA CCTAAATAGA GATAAAATC                                             29

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:14:

GTTTACCGCA CCTACGTCGA CCCTGTGTAG CCTTGA                                  36

(2) INFORMATION FOR SEQ ID NO:15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:15:

TCAAGGCTAC ACAGGGTCGA CGTAGGTGCG GTAAAC                                  36

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:16:

GCAAGCTTGA CAGAGAACAG AGAAGCCAG                                          29

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:17:

CGTCGACGCC TTTGCGGTAG TGGTGCTT                                           28

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:18:

CGCGGCCGCA GGCCCTTAAG GCCAGAACCA AATGAA                                  36

(2) INFORMATION FOR SEQ ID NO:19:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:19:

TGGCCTTAAG GGCCTGCGGC CGCGATTTCC AATG                                    34

(2) INFORMATION FOR SEQ ID NO:20:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:20:

```
GAAGCTTCTT CATCATCATT GGCATACG                                              28

(2) INFORMATION FOR SEQ ID NO:21:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:21:

AAGCTTTGAA TGGGTGTGG                                                        19

(2) INFORMATION FOR SEQ ID NO:22:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:22:

CCGCTTGTTC TTTCATCCCC TGAAACAACT GTACCG                                     36

(2) INFORMATION FOR SEQ ID NO:23:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:23:

CAGTTGTTTC AGGGGATGAA AGAACAAGCG GCTG                                       34

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:24:

CTGACATGAG GCACTGAC                                                         18

(2) INFORMATION FOR SEQ ID NO:25:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:25:

TTTGGCCTTA AGGGCCTGCA ATCGATTGTT TGAGAAAAGA AG                              42

(2) INFORMATION FOR SEQ ID NO:26:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:26:

TTTGAGCTCC ATTTTCTTAT ACAAATTATA TTTTACATAT CAG                             43
```

(2) INFORMATION FOR SEQ ID NO:27:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO:27:

```
AGCTAGGCCT TAAGGGCCCG GGACGTCGAG CTCAAGCTTG CGGCCGCCAT GGTCGACG        58
```

(2) INFORMATION FOR SEQ ID NO:28:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:28:

```
AATTCGTCGA CCATGGCGGC CGCAAGCTTG AGCTCGACGT CCCGGGCCCT TAAGGCC        57
```

(2) INFORMATION FOR SEQ ID NO:29:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:29:

```
CTGAGCTCTA CGAAAGGAGA CACACATGC                                       29
```

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:30:

```
ACGCCCAGCT GTTTAAGATA AG                                              22
```

(2) INFORMATION FOR SEQ ID NO:31:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:31:

```
AGCTTGGCCT TAAGGGCCCG ATATCGGATC CGCGGCCGCT GCAGGTAC                  48
```

(2) INFORMATION FOR SEQ ID NO:32:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:32:

```
CTGCAGCGGC CGCGGATCCG ATATCGGGCC CTTAAGGCCA                            40
```

(2) INFORMATION FOR SEQ ID NO:33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:33:

GCGGCCGCGA TTTCCAATGA G          21

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

GGTACCTGCA TTTGCCAGCA C          21

(2) INFORMATION FOR SEQ ID NO:35:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 3...6
        (D) OTHER INFORMATION: Xaa at positions 3 and 6 are D-Leu (xi) SEQUENCE DESCRIPTION: SEQ ID NO:35:

Glu Leu Xaa Val Asp Xaa Leu
1          5